United States Patent
Lynch et al.

(10) Patent No.: US 6,552,166 B1
(45) Date of Patent: Apr. 22, 2003

(54) PROCESS FOR THE PREPARATION OF CONJUGATES USEFUL IN THE TREATMENT OF PROSTATE CANCER

(75) Inventors: Joseph E. Lynch, Plainfield, NJ (US); Michael A. Robbins, Short Hills, NJ (US); Yao-Jun Shi, Edison, NJ (US); David R. Lieberman, Jersey City, NJ (US)

(73) Assignee: Merck & Co., Inc., Rahway, NJ (US)

( * ) Notice: Subject to any disclaimer, the term of this patent is extended or adjusted under 35 U.S.C. 154(b) by 170 days.

(21) Appl. No.: 09/691,523

(22) Filed: Oct. 18, 2000

Related U.S. Application Data

(60) Provisional application No. 60/160,361, filed on Oct. 19, 1999.

(51) Int. Cl.⁷ ............... C07K 1/10; C07K 1/113; C07K 9/00
(52) U.S. Cl. ............. 530/322; 530/338; 530/345
(58) Field of Search ............... 514/8, 16, 34; 530/322, 329, 338, 340, 341, 345; 536/6.4

(56) References Cited

U.S. PATENT DOCUMENTS

| | | | |
|---|---|---|---|
| 4,277,466 A | 7/1981 | Trouet | 514/34 |
| 4,296,105 A | 10/1981 | Baurain et al. | 514/34 |
| 4,703,107 A | 10/1987 | Monsigny et al. | 530/330 |
| 5,712,418 A | * 1/1998 | Carpino et al. | 564/225 |
| 5,866,679 A | 2/1999 | DeFeo-Jones et al. | 530/322 |
| 6,355,611 B1 | * 3/2002 | Karki et al. | 514/8 |
| 2002/0042375 A1 | * 4/2002 | Heimbrook et al. | 514/16 |

FOREIGN PATENT DOCUMENTS

| | | |
|---|---|---|
| WO | 98/10651 | * 3/1998 |
| WO | WO 98/18493 | 5/1998 |
| WO | WO 98/52966 | 11/1998 |
| WO | WO 00/59930 | 10/2000 |
| WO | WO 01/29065 A1 | 4/2001 |
| WO | WO 01/30804 A2 | 5/2001 |

OTHER PUBLICATIONS

Israel et al., Adriamycin Analogues. Preparation and Biological Evaluation of Some N–(Trifluoracetyl)–14–O–[(N–acetylamino)acyl]adriamycin Derivatives, J. Med. Chem., 1986, vol. 29, No. 7, pp. 1273–1276.

Masquelier et al., Amino Acid and Dipeptide Derivatives of Daunorubicin. 1. Synthesis, Physicochemical Properties, and Lysosomal Digestion, J. Med. Chem., 1980, vol. 23, No. 11, pp. 1166–1170.

Seitz et al., Synthesis and Chemical Properties of a Series of Doxorubicin Enaminomalonyl–β–Alanine Derivatives, Tetrahedron Letters, 1995, vol. 36, No. 9, pp. 1413–1416.

Chakravarty et al., Plasmin–Activated Prodrugs for Cancer Chemotherapy. 2. Synthesis and Biological Activity of Peptidyl Derivatives of Doxorubicin, J. Med. Chem., 1983, vol. 26, No. 5, pp. 638–644.

Carpino, 1–Hydroxy–7–azabenzotriazole. An Efficient Peptide Coupling Additive, J. Am. Chem. Soc., 1993, vol. 115, No. 10, pp. 4397–4398.

Carpino et al., Efficiency in Peptide Coupling: 1–Hydroxy–7–azabenzotriazole vs 3,4–Dihydro–3–hydroxy–4–oxo–1,2,3–benzotriazine, J. Org. Chem., 1995, vol. 60, No. 11, pp. 3561–3564.

Ho et al., Carbodiimide–Mediated Amide Formation in a Two–Phase System. A High–Yield and Low–Racemization Procedure for Peptide Synthesis. J. Org. Chem., 1995, vol. 60, No. 11, pp. 3569–3560.

Carpino et al., Effect of Tertiary Bases on O–Benzotriazolyluronium Salt–Induced Peptide Segment Coupling, The Journal of Organic Chemistry, Feb. 1994, vol. 59, No. 4, pp. 695–698.

* cited by examiner

Primary Examiner—Jeffrey E. Russel
(74) Attorney, Agent, or Firm—David A. Muthard; Mark R. Daniel

(57) ABSTRACT

The present invention is directed to the improved synthesis of compounds of formula I:

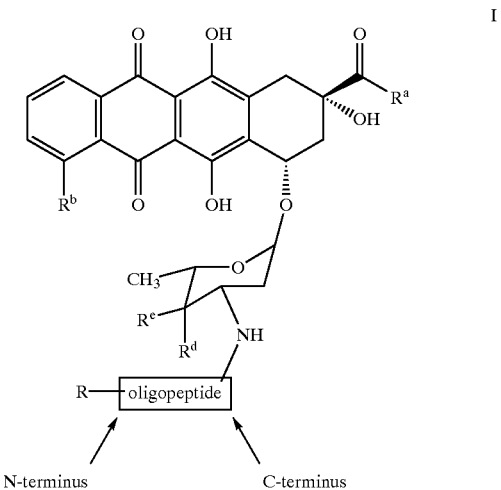

which may be useful in the treatment of prostate cancer. Such compounds are synthesized in the presence of a carboxyl activating agent, an additive and a base for the preparation of a PSA conjugate which comprises an anthracycline antibiotic and an oligopeptide.

35 Claims, No Drawings

SEQUENCE LISTING

```
<160> NUMBER OF SEQ ID NOS: 69

<210> SEQ ID NO 1
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid

<400> SEQUENCE: 1

Pro Xaa Ser Tyr Gln Ser Ser
 1               5

<210> SEQ ID NO 2
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid

<400> SEQUENCE: 2

Pro Xaa Ser Tyr Gln Ser Ala
 1               5

<210> SEQ ID NO 3
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (2)...(2)
<223> OTHER INFORMATION: 4-hydroxyproline
<221> NAME/KEY: VARIANT
<222> LOCATION: (3)...(3)
<223> OTHER INFORMATION: Xaa = any amino acid

<400> SEQUENCE: 3

Ala Pro Xaa Ser Tyr Tyr Ser
 1               5

<210> SEQ ID NO 4
<211> LENGTH: 8
<212> TYPE: PRT
<213> ORGANISM: Artificial Sequence
```

```
<220> FEATURE:
<223> OTHER INFORMATION: Completely Synthetic Amino Acid Sequence
<221> NAME/KEY: VARIANT
<222> LOCATION: (3)...(3)
<223> OTHER INFORMATION: 4-hydroxyproline
<221> NAME/KEY: VARIANT
<222> LOCATION: (4)...(4)
<223> OTHER INFORMATION: Xaa = any amino acid

<400> SEQUENCE: 4

Ala Asn Pro Xaa Ser Tyr Gln Ser
 1               5

<210> SEQ ID NO 5
<211> LENGTH: 8
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid

<400> SEQUENCE: 5

Pro Xaa Ser Tyr Gln Ser Ser Thr
 1               5

<210> SEQ ID NO 6
<211> LENGTH: 6
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline

<400> SEQUENCE: 6

Pro Tyr Gln Ser Ser Thr
 1               5

<210> SEQ ID NO 7
<211> LENGTH: 8
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid

<400> SEQUENCE: 7

Pro Xaa Ser Tyr Gln Ser Ser Ser
 1               5

<210> SEQ ID NO 8
<211> LENGTH: 6
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
```

```
<400> SEQUENCE: 8

Pro Tyr Gln Ser Ser Ser
 1               5

<210> SEQ ID NO 9
<211> LENGTH: 8
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid

<400> SEQUENCE: 9

Pro Xaa Lys Tyr Gln Ser Ser Ser
 1               5

<210> SEQ ID NO 10
<211> LENGTH: 8
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid
<221> NAME/KEY: VARIANT
<222> LOCATION: (3)...(3)
<223> OTHER INFORMATION: Xaa = homoarginine

<400> SEQUENCE: 10

Pro Xaa Xaa Tyr Gln Ser Ser Ser
 1               5

<210> SEQ ID NO 11
<211> LENGTH: 8
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid

<400> SEQUENCE: 11

Pro Xaa Ser Tyr Gln Ser Ser Leu
 1               5

<210> SEQ ID NO 12
<211> LENGTH: 6
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline

<400> SEQUENCE: 12

Pro Tyr Gln Ser Ser Leu
```

-continued

```
1               5

<210> SEQ ID NO 13
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid

<400> SEQUENCE: 13

Pro Xaa Ser Tyr Gln Ser Leu
 1               5

<210> SEQ ID NO 14
<211> LENGTH: 5
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline

<400> SEQUENCE: 14

Pro Tyr Gln Ser Leu
 1               5

<210> SEQ ID NO 15
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid
<221> NAME/KEY: VARIANT
<222> LOCATION: (7)...(7)
<223> OTHER INFORMATION: norleucine

<400> SEQUENCE: 15

Pro Xaa Ser Tyr Gln Ser Leu
 1               5

<210> SEQ ID NO 16
<211> LENGTH: 5
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (5)...(5)
<223> OTHER INFORMATION: norleucine

<400> SEQUENCE: 16

Pro Tyr Gln Ser Leu
 1               5
```

```
<210> SEQ ID NO 17
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (2)...(2)
<223> OTHER INFORMATION: Xaa = any amino acid
<221> NAME/KEY: VARIANT
<222> LOCATION: (7)...(7)
<223> OTHER INFORMATION: Xaa = 1,2,3,4-tetrahydro-3-isoquinoline
      carboxylic acid
<221> NAME/KEY: VARIANT
<222> LOCATION: (1)...(1)
<223> OTHER INFORMATION: 4-hydroxyproline

<400> SEQUENCE: 17

Pro Xaa Ser Tyr Gln Ser Xaa
 1               5

<210> SEQ ID NO 18
<211> LENGTH: 5
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (5)...(5)
<223> OTHER INFORMATION: Xaa = 1,2,3,4-tetrahydro-3-isoquinoline
      carboxylic acid

<400> SEQUENCE: 18

Pro Tyr Gln Ser Xaa
 1               5

<210> SEQ ID NO 19
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid
<221> NAME/KEY: VARIANT
<222> LOCATION: (4)...(4)
<223> OTHER INFORMATION: Xaa = cyclohexylglycine

<400> SEQUENCE: 19

Pro Xaa Ser Xaa Gln Ser Leu
 1               5

<210> SEQ ID NO 20
<211> LENGTH: 5
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = cyclohexyglycine

<400> SEQUENCE: 20
```

Pro Xaa Gln Ser Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = any amino acid
<221> NAME/KEY: VARIANT
<222> LOCATION: (4)...(4)
<223> OTHER INFORMATION: Xaa = cyclohexylglycine
<221> NAME/KEY: VARIANT
<222> LOCATION: (7)...(7)
<223> OTHER INFORMATION: norleucine

<400> SEQUENCE: 21

Pro Xaa Ser Xaa Gln Ser Leu
1               5

<210> SEQ ID NO 22
<211> LENGTH: 5
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = cyclohexylglycine
<221> NAME/KEY: VARIANT
<222> LOCATION: (5)...(5)
<223> OTHER INFORMATION: norleucine

<400> SEQUENCE: 22

Pro Xaa Gln Ser Leu
1               5

<210> SEQ ID NO 23
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (4)...(4)
<223> OTHER INFORMATION: Xaa = cyclohexylglycine
<221> NAME/KEY: VARIANT
<222> LOCATION: (7)...(7)
<223> OTHER INFORMATION: Xaa = 1,2,3,4-tetrahydro-3-isoquinoline
    carboxylic acid
<221> NAME/KEY: VARIANT
<222> LOCATION: (2)...(2)
<223> OTHER INFORMATION: Xaa = any amino acid

<400> SEQUENCE: 23

Pro Xaa Ser Xaa Gln Ser Xaa
1               5

<210> SEQ ID NO 24

```
<211> LENGTH: 5
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: 4-hydroxyproline
<221> NAME/KEY: VARIANT
<222> LOCATION: (2)...(2)
<223> OTHER INFORMATION: Xaa = cyclohexylglycine
<221> NAME/KEY: VARIANT
<222> LOCATION: (5)...(5)
<223> OTHER INFORMATION: Xaa = 1,2,3,4-tetrahydro-3-isoquinoline
      carboxylic acid

<400> SEQUENCE: 24

Pro Xaa Gln Ser Xaa
 1               5

<210> SEQ ID NO 25
<211> LENGTH: 7
<212> TYPE: PRT
<213> ORGANISM: Artificial Sequence
<220> FEATURE:
<223> OTHER INFORMATION: Completely Synthetic Amino Acid Sequence

<400> SEQUENCE: 25

Ala Ser Tyr Gln Ser Ser Leu
 1               5

<210> SEQ ID NO 26
<211> LENGTH: 6
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (2)...(2)
<223> OTHER INFORMATION: Xaa = homoarginine
<221> NAME/KEY: VARIANT
<222> LOCATION: (3)...(3)
<223> OTHER INFORMATION: Xaa = cyclohexylglycine

<400> SEQUENCE: 26

Ser Xaa Xaa Gln Ser Leu
 1               5

<210> SEQ ID NO 27
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (7)...(7)
<223> OTHER INFORMATION: norleucine

<400> SEQUENCE: 27

Xaa Ser Ser Tyr Gln Ser Leu
 1               5

<210> SEQ ID NO 28
<211> LENGTH: 7
<212> TYPE: PRT
<213> ORGANISM: Artificial Sequence
<220> FEATURE:
<223> OTHER INFORMATION: Completely Synthetic Amino Acid Sequence
```

```
<221> NAME/KEY: VARIANT
<222> LOCATION: (1)...(1)
<223> OTHER INFORMATION: Xaa = homoarginine
<221> NAME/KEY: VARIANT
<222> LOCATION: (4)...(4)
<223> OTHER INFORMATION: Xaa = cyclohexylglycine

<400> SEQUENCE: 28

Xaa Ala Ser Xaa Gln Ser Leu
 1               5

<210> SEQ ID NO 29
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = homoarginine

<400> SEQUENCE: 29

Xaa Ser Ser Tyr Gln Ser Leu
 1               5

<210> SEQ ID NO 30
<211> LENGTH: 6
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (4)...(4)
<223> OTHER INFORMATION: Xaa = cyclohexylglycine

<400> SEQUENCE: 30

Xaa Ser Ser Xaa Ser Leu
 1               5

<210> SEQ ID NO 31
<211> LENGTH: 6
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (2)...(2)
<223> OTHER INFORMATION: Xaa = homoarginine
<221> NAME/KEY: VARIANT
<222> LOCATION: (3)...(3)
<223> OTHER INFORMATION: Xaa = cyclohexylglycine

<400> SEQUENCE: 31

Ser Xaa Xaa Gln Ser Leu
 1               5

<210> SEQ ID NO 32
<211> LENGTH: 5
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = homoarginine

<400> SEQUENCE: 32
```

```
Xaa Tyr Gln Ser Leu
 1               5

<210> SEQ ID NO 33
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (4)...(4)
<223> OTHER INFORMATION: Xaa = cyclohexylglycine

<400> SEQUENCE: 33

Xaa Ser Ser Xaa Gln Ser Leu
 1               5

<210> SEQ ID NO 34
<211> LENGTH: 6
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (2)...(2)
<223> OTHER INFORMATION: Xaa = homoarginine

<400> SEQUENCE: 34

Ser Xaa Tyr Gln Ser Leu
 1               5

<210> SEQ ID NO 35
<211> LENGTH: 6
<212> TYPE: PRT
<213> ORGANISM: Artificial Sequence
<220> FEATURE:
<223> OTHER INFORMATION: Completely Synthetic Amino Acid Sequence

<400> SEQUENCE: 35

Ser Ser Tyr Gln Ser Leu
 1               5

<210> SEQ ID NO 36
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (4)...(4)
<223> OTHER INFORMATION: Xaa = cyclohexylglycine

<400> SEQUENCE: 36

Ser Ser Ser Xaa Gln Ser Leu
 1               5

<210> SEQ ID NO 37
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = 3-pyridylalanine
<221> NAME/KEY: VARIANT
<222> LOCATION: (4)...(4)
```

<223> OTHER INFORMATION: Xaa = cyclohexylglycine

<400> SEQUENCE: 37

Xaa Ser Ser Xaa Gln Ser Leu
 1               5

<210> SEQ ID NO 38
<211> LENGTH: 6
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (3)...(3)
<223> OTHER INFORMATION: Xaa = cyclohexylglycine

<400> SEQUENCE: 38

Ser Ser Xaa Gln Ser Leu
 1               5

<210> SEQ ID NO 39
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (4)...(4)
<223> OTHER INFORMATION: Xaa = cyclohexylglycine
<221> NAME/KEY: VARIANT
<222> LOCATION: (7)...(7)
<223> OTHER INFORMATION: unnatural configuration amino acid

<400> SEQUENCE: 39

Ser Ser Ser Xaa Gln Ser Leu
 1               5

<210> SEQ ID NO 40
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (4)...(4)
<223> OTHER INFORMATION: Xaa = cyclohexylglycine

<400> SEQUENCE: 40

Ser Ser Ser Xaa Gln Ser Val
 1               5

<210> SEQ ID NO 41
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (4)...(4)
<223> OTHER INFORMATION: Xaa = cyclohexylglycine

<400> SEQUENCE: 41

Pro Ser Ser Xaa Gln Ser Val
 1               5

<210> SEQ ID NO 42
<211> LENGTH: 7
<212> TYPE: PRT
<213> ORGANISM: Artificial Sequence

```
<220> FEATURE:
<223> OTHER INFORMATION: Completely Synthetic Amino Acid Sequence
<221> NAME/KEY: VARIANT
<222> LOCATION: (4)...(4)
<223> OTHER INFORMATION: Xaa = cyclohexylglycine

<400> SEQUENCE: 42

Gly Ser Ser Xaa Gln Ser Leu
 1               5

<210> SEQ ID NO 43
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = homoserine
<221> NAME/KEY: VARIANT
<222> LOCATION: (4)...(4)
<223> OTHER INFORMATION: Xaa = cyclohexylglycine

<400> SEQUENCE: 43

Xaa Ser Ser Xaa Gln Ser Leu
 1               5

<210> SEQ ID NO 44
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (4)...(4)
<223> OTHER INFORMATION: Xaa = cyclohexylglycine
<221> NAME/KEY: VARIANT
<222> LOCATION: (7)...(7)
<223> OTHER INFORMATION: norleucine

<400> SEQUENCE: 44

Xaa Ser Ser Xaa Gln Ser Leu
 1               5

<210> SEQ ID NO 45
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = homoarginine

<400> SEQUENCE: 45

Xaa Tyr Gln Ser Ser Ser Leu
 1               5

<210> SEQ ID NO 46
<211> LENGTH: 7
<212> TYPE: PRT
<213> ORGANISM: Artificial Sequence
<220> FEATURE:
<223> OTHER INFORMATION: Completely Synthetic Amino Acid Sequence

<400> SEQUENCE: 46

Lys Tyr Gln Ser Ser Ser Leu
```

```
                    1               5

<210> SEQ ID NO 47
<211> LENGTH: 7
<212> TYPE: PRT
<213> ORGANISM: Artificial Sequence
<220> FEATURE:
<223> OTHER INFORMATION: Completely Synthetic Amino Acid Sequence

<400> SEQUENCE: 47

Ser Tyr Gln Ser Ser Ser Leu
  1               5

<210> SEQ ID NO 48
<211> LENGTH: 6
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (3)...(3)
<223> OTHER INFORMATION: Xaa = cyclohexylglycine
<221> NAME/KEY: VARIANT
<222> LOCATION: (6)...(6)
<223> OTHER INFORMATION: unnatural configuration amino acid

<400> SEQUENCE: 48

Ser Ser Xaa Gln Ser Leu
  1               5

<210> SEQ ID NO 49
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = 3-pyridylalanine
<221> NAME/KEY: VARIANT
<222> LOCATION: (4)...(4)
<223> OTHER INFORMATION: Xaa = cyclohexylglycine
<221> NAME/KEY: VARIANT
<222> LOCATION: (7)...(7)
<223> OTHER INFORMATION: unnatural configuration amino acid

<400> SEQUENCE: 49

Xaa Ser Ser Xaa Gln Ser Leu
  1               5

<210> SEQ ID NO 50
<211> LENGTH: 6
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (3)...(3)
<223> OTHER INFORMATION: Xaa = cyclohexylglycine

<400> SEQUENCE: 50

Ala Ser Xaa Gln Ser Leu
  1               5

<210> SEQ ID NO 51
<211> LENGTH: 7
<212> TYPE: PRT
<213> ORGANISM: Artificial Sequence
<220> FEATURE:
<223> OTHER INFORMATION: Completely Synthetic Amino Acid Sequence
```

```
<221> NAME/KEY: VARIANT
<222> LOCATION: (1)...(1)
<223> OTHER INFORMATION: Xaa = N-(glutaryl)4-trans-hydroxy-L-proline
<221> NAME/KEY: VARIANT
<222> LOCATION: (4)...(4)
<223> OTHER INFORMATION: Xaa = cyclohexylglycine

<400> SEQUENCE: 51

Xaa Ala Ser Xaa Gln Ser Leu
 1               5

<210> SEQ ID NO 52
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa =
      4-(fluorenylmethoxyglutaryl)-4-trans-hydroxy-L-pro
      line
<221> NAME/KEY: VARIANT
<222> LOCATION: (4)...(4)
<223> OTHER INFORMATION: Xaa = cyclohexylglycine

<400> SEQUENCE: 52

Xaa Ala Ser Xaa Gln Ser Leu
 1               5

<210> SEQ ID NO 53
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = homoarginine
<221> NAME/KEY: VARIANT
<222> LOCATION: (3)...(3)
<223> OTHER INFORMATION: 4-hydroxyproline
<221> NAME/KEY: VARIANT
<222> LOCATION: (4)...(4)
<223> OTHER INFORMATION: Xaa = cyclohexylglycine

<400> SEQUENCE: 53

Xaa Ser Pro Xaa Gln Ser Leu
 1               5

<210> SEQ ID NO 54
<211> LENGTH: 5
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = 4-hydroxyproline
<221> NAME/KEY: VARIANT
<222> LOCATION: (2)...(2)
<223> OTHER INFORMATION: Xaa = cyclohexylglycine

<400> SEQUENCE: 54

Xaa Xaa Gln Ser Leu
 1               5

<210> SEQ ID NO 55
<211> LENGTH: 7
<212> TYPE: PRT
<213> ORGANISM: Artificial Sequence
```

```
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-(acetyl)-4-hydroxy proline
<221> NAME/KEY: VARIANT
<222> LOCATION: (4)...(4)
<223> OTHER INFORMATION: Xaa = cyclohexylglycine

<400> SEQUENCE: 55

Xaa Ala Ser Xaa Gln Ser Leu
 1               5

<210> SEQ ID NO 56
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-succinyl-4-hydroxyproline
<221> NAME/KEY: VARIANT
<222> LOCATION: (4)...(4)
<223> OTHER INFORMATION: Xaa = cyclohexylglycine

<400> SEQUENCE: 56

Xaa Ala Ser Xaa Gln Ser Leu
 1               5

<210> SEQ ID NO 57
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-acetyl-3,4-dihydroxy proline
<221> NAME/KEY: VARIANT
<222> LOCATION: (4)...(4)
<223> OTHER INFORMATION: Xaa = cyclohexylglycine

<400> SEQUENCE: 57

Xaa Ala Ser Xaa Gln Ser Leu
 1               5

<210> SEQ ID NO 58
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-(PEG-2)acetyl)-4-hydroxyproline
<221> NAME/KEY: VARIANT
<222> LOCATION: (4)...(4)
<223> OTHER INFORMATION: Xaa = cyclohexylglycine

<400> SEQUENCE: 58

Xaa Ala Ser Xaa Gln Ser Leu
 1               5

<210> SEQ ID NO 59
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
```

```
<222> LOCATION: (1)...(1)
<223> OTHER INFORMATION: Xaa = N-glutaryl-4-hydroxyproline
<221> NAME/KEY: VARIANT
<222> LOCATION: (4)...(4)
<223> OTHER INFORMATION: Xaa = cyclohexylglycine
<221> NAME/KEY: VARIANT
<222> LOCATION: (7)...(7)
<223> OTHER INFORMATION: Xaa = t-butyl alanine

<400> SEQUENCE: 59

Xaa Ala Ser Xaa Gln Ser Xaa
 1               5

<210> SEQ ID NO 60
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-glutaryl-4-hydroxy-proline
<221> NAME/KEY: VARIANT
<222> LOCATION: (4)...(4)
<223> OTHER INFORMATION: Xaa = cyclohexylglycine

<400> SEQUENCE: 60

Xaa Ser Ser Xaa Gln Ser Leu
 1               5

<210> SEQ ID NO 61
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-(PEG-2-acetyl)-4-hydroxyproline
<221> NAME/KEY: VARIANT
<222> LOCATION: (4)...(4)
<223> OTHER INFORMATION: Xaa = cyclohexylglycine

<400> SEQUENCE: 61

Xaa Ser Ser Xaa Gln Ser Leu
 1               5

<210> SEQ ID NO 62
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-(2R)(2,3-dihydroxypropionyl)serine
<221> NAME/KEY: VARIANT
<222> LOCATION: (4)...(4)
<223> OTHER INFORMATION: Xaa = cyclohexylglycine

<400> SEQUENCE: 62

Xaa Ser Ser Xaa Gln Ser Leu
 1               5

<210> SEQ ID NO 63
<211> LENGTH: 4
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
```

```
<222> LOCATION: (1)...(1)
<223> OTHER INFORMATION: Xaa = cyclohexylglycine
<221> NAME/KEY: VARIANT
<222> LOCATION: (4)...(4)
<223> OTHER INFORMATION: leucine benzylester

<400> SEQUENCE: 63

Xaa Gln Ser Leu
 1

<210> SEQ ID NO 64
<211> LENGTH: 4
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-butoxycarbonyl cyclohexylglycine
<221> NAME/KEY: VARIANT
<222> LOCATION: (4)...(4)
<223> OTHER INFORMATION: leucine benzylester

<400> SEQUENCE: 64

Xaa Gln Ser Leu
 1

<210> SEQ ID NO 65
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION:
      4-(fluorenylmethoxyglutaryl)-4-trans-hydroxy-L-proline
<221> NAME/KEY: VARIANT
<222> LOCATION: (4)...(4)
<223> OTHER INFORMATION: Xaa = cyclohexylglycine
<221> NAME/KEY: VARIANT
<222> LOCATION: (7)...(7)
<223> OTHER INFORMATION: leucine benzylester

<400> SEQUENCE: 65

Pro Ala Ser Xaa Gln Ser Leu
 1               5

<210> SEQ ID NO 66
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-hydroxyacetylserine
<221> NAME/KEY: VARIANT
<222> LOCATION: (4)...(4)
<223> OTHER INFORMATION: Xaa = cyclohexylglycine
```

```
<400> SEQUENCE: 66

Xaa Ser Ser Xaa Gln Ser Leu
 1               5

<210> SEQ ID NO 67
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: N-(4-benzylglutaryl)-4-trans-hydroxy-L-proline
<221> NAME/KEY: VARIANT
<222> LOCATION: (4)...(4)
<223> OTHER INFORMATION: Xaa = cyclohexylglycine
<221> NAME/KEY: VARIANT
<222> LOCATION: (7)...(7)
<223> OTHER INFORMATION: leucine fluorenylmethoxyester

<400> SEQUENCE: 67

Pro Ala Ser Xaa Gln Ser Leu
 1               5

<210> SEQ ID NO 68
<211> LENGTH: 7
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: N-(4-benzylglutaryl)-4-trans-hydroxy-L-proline
<221> NAME/KEY: VARIANT
<222> LOCATION: (4)...(4)
<223> OTHER INFORMATION: Xaa = cyclohexylglycine

<400> SEQUENCE: 68

Pro Ala Ser Xaa Glu Ser Leu
 1               5

<210> SEQ ID NO 69
<211> LENGTH: 4
<212> TYPE: PRT
<213> ORGANISM: Artificial Sequence
<220> FEATURE:
<223> OTHER INFORMATION: Completely Synthetic Amino Acid Sequence
<221> NAME/KEY: VARIANT
<222> LOCATION: (1)...(1)
<223> OTHER INFORMATION: Xaa = N-protected cyclohexyl glycine

<400> SEQUENCE: 69

Xaa Glu Ser Leu
 1
```

PROCESS FOR THE PREPARATION OF CONJUGATES USEFUL IN THE TREATMENT OF PROSTATE CANCER

RELATED APPLICATIONS

This application, under 35 U.S.C. §119(e), claims the benefit of U.S. Provisional Application No. 60/160,361, filed Oct. 19, 1999.

BACKGROUND OF THE INVENTION

In 1994 cancer of the prostate gland is expected to be diagnosed in 200,000 men in the U.S. and 38,000 American males will die from this disease (Garnick, M. B. (1994). The Dilemmas of Prostate Cancer. Scientific American, April:72–81). Thus, prostate cancer is the most frequently diagnosed malignancy (other than that of the skin) in U.S. men and the second leading cause of cancer-related deaths (behind lung cancer) in that group.

Compositions useful in the treatment of prostatic cancer and related conditions are described in U.S. Pat. Nos. 5,599,686, 5,866,679 and 5,948,750, and U.S. patent applications Ser. No. 08/950,805, filed Oct. 14, 1997, now U.S. Pat. No. 8,948,750, (PCT Publ.No. WO 98/18493). Said compositions comprise chemical conjugates comprising known cytotoxic agents and oligopeptides having amino acid sequences that are selectively proteolytically cleaved by free prostate specific antigen and that include a cyclic amino acid having a hydrophilic substituent. The oligopeptide moieties are selected from oligomers that are selectively recognised by free prostate specific antigen (PSA) and are capable of being proteolytically cleaved by the enzymatic activity thereof.

Ideally, the cytotoxic activity of the cytotoxic agent is greatly reduced or absent when the intact oligopeptide containing the PSA proteolytic cleavage site is bonded directly, or through a chemical linker, to the cytotoxic agent. Also ideally, the cytotoxic activity of the cytotoxic agent increases significantly, or is restored completely, upon proteolytic cleavage of the attached oligopeptide at the cleavage site. Anthracycline antibiotics, in particular doxorubicin, are among the cytotoxic agents that were described in the published patent applications as preferably incorporated into such conjugates, which may be referred to as PSA conjugates.

It is the object of this invention to provide an efficient, scaleable and reproducible process for the preparation of PSA conjugates having an anthracycline antibiotic moiety as the cytotoxic agent and having the cleavable oligopeptide directly attached, via the C-terminus amino acid, to the glycosyl amine of the anthracycline antibiotic moiety.

Another object of this invention is to provide intermediate compounds useful in the preparation of such PSA conjugates.

SUMMARY OF THE INVENTION

A chemical process for the preparation of a PSA conjugate which comprises an anthracycline antibiotic and an oligopeptide, having an amino acid sequence that is selectively proteolytically cleaved by free prostate specific antigen (PSA) is disclosed. Such conjugates are useful in the treatment of prostatic cancer and benign prostatic hyperplasia (BPH).

DETAILED DESCRIPTION OF THE INVENTION

The present invention is directed to a process for the preparation of compounds as illustrated by formula I:

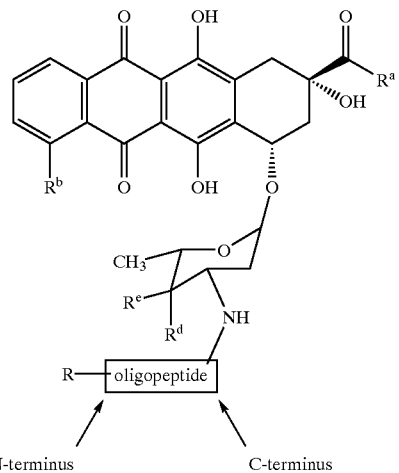

or a pharmaceutically acceptable salt thereof
wherein
oligopeptide is an oligopeptide which is selectively recognized by the free prostate specific antigen (PSA) and is capable of being proteolytically cleaved by the enzymatic activity of the free prostate specific antigen,
$R^a$ is —$CH_3$, —$CH_2OH$, —$CH_2OCO(CH_2)_3CH_3$, or —$CH_2OCOCH(OC_2H_5)_2$;
$R^b$ is —$OCH_3$, —OH or —H;
$R^d$ is —OH, —OTHP or —H; and
$R^e$ is —OH or —H, provided that $R^e$ is not —OH when $R^d$ is —OH or —OTHP;
R is selected from:
a) acetyl;

b)

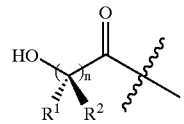

c)

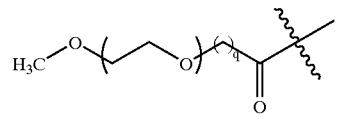

d)

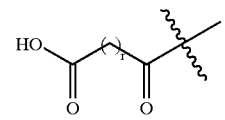

e) hydrogen;
$R^1$ and $R^2$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^3O$—, $R^3C(O)NR^3$—, $(R^3)_2NC(O)$—, $R^3_2N$—$C(NR^3)$—, $R^4S(O)_mNH$, CN, $NO_2$, $R^3C(O)$—, $N_3$, —$N(R^3)_2$, or $R^4C(O)NR^3$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^3O$—, $R^4S(O)_mNH$, $R^3C(O)NR^3$—, $(R^3)_2NC(O)$—, $R^3_2N$—$C(NR^3)$—, CN, $R^3C(O)$—, $N_3$, —$N(R^3)_2$, and $R^4OC(O)$—$NR^3$—; or $R^1$ and $R^2$ are combined to form —$(CH_2)_s$— wherein one of the carbon atoms is optionally replaced by a moiety selected from: O, $S(O)_m$, —$NC(O)$—, NH and —$N(COR^4)$—;

$R^3$ is selected from: hydrogen, aryl, substituted aryl, heterocycle, substituted heterocycle, $C_1$–$C_6$ alkyl and $C_3$–$C_{10}$ cycloalkyl;

$R^4$ is selected from: aryl, substituted aryl, heterocycle, substituted heterocycle, $C_1$–$C_6$ alkyl and $C_3$–$C_{10}$ cycloalkyl;

m is 0, 1 or 2;

n is 1, 2, 3 or 4;

p is zero or an integer between 1 and 100;

q is 0 or 1, provided that if p is zero, q is 1;

r is an integer between 1 and 10; and s is 3, 4 or 5.

The process comprises the step of preparing the compound of the formula Ia:

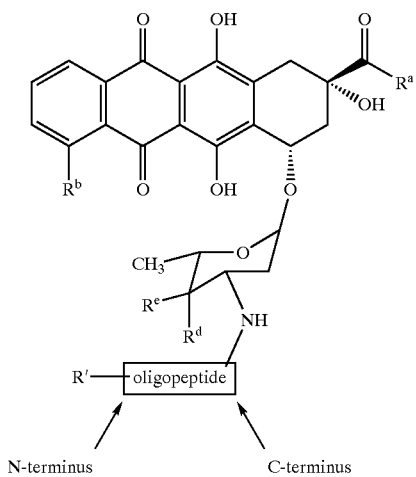

Ia or a salt thereof;

wherein oligopeptide, R, $R^a$, $R^b$, $R^d$ and $R^e$ are described as above

R' is selected from:
a) R,
b) a protected precursor to R, and
c) an N-terminus protecting group;

by mixing an oligopeptide of the formula A:

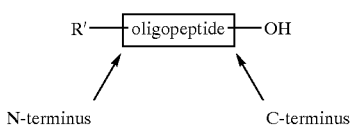

A wherein oligopeptide and R' are described as above, or a salt thereof;

with an anthracycline antibiotic of the formula B:

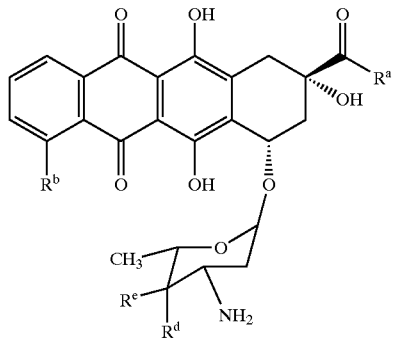

B or a salt thereof, wherein $R^a$, $R^b$, $R^d$ and $R^e$ are as described hereinabove, in the presence of a carboxyl activating agent and, optionally, in the presence of a base.

In an embodiment of the instant process, if R' is a protected precursor to R or an N-terminus protecting group, the process further comprises the step of removing the protecting group to produce the compound of the formula I.

In an embodiment of the instant process, the oligopeptide of formula A is mixed with a salt of the anthracycline antibiotic of the formula B in the presence of a carboxyl activating agent and a base.

In an embodiment of the instant process, the carboxyl activating agent is selected from dicyclohexylcarbodiimide (DCC), N-ethyl-N-(3-dimethylaminopropyl)-carbodiimide (EDC), and 1,3-diisopropylcarbodiimide (DIC).

In a preferred embodiment, the carboxyl activating agent is EDC.

In an embodiment of the instant process, the base is selected from 2,4,6-collidine, lutidine, pyridine, triethyl amine and $(iPr)_2NEt$.

In a preferred embodiment, the base is 2,4,6-collidine.

It has been surprisingly discovered that use 2,4,6-collidine as the base in the instant process for the formation of the compound of the formula Ia results in lower epimerization of the C-terminus amino acid moiety than when other bases previously described are utilized.

In a further embodiment of the instant process, the mixing of the compounds of formula A and formula B is additionally in the presence of an additive.

In a preferred further embodiment of the instant process the additive is selected from HOAt, HOBt, HOPO or a combination thereof.

In a preferred embodiment of the further embodiment of the instant process, the additive is HOAt.

In a second preferred embodiment of the further embodiment of the instant process, the additive is a combination of HOPO and HOAt.

In a further embodiment of the instant process, the oligopeptide of the formula A is mixed with the anthracycline antibiotic of the formula B in the presence of a carboxyl activating agent, an additive and a base.

In a preferred further embodiment of the instant process, the oligopeptide of the formula A is mixed with the anthracycline antibiotic of the formula B in the presence of an additive and a base, and a carboxyl activating agent is thereafter added to the mixture.

It has been surprisingly discovered that when the carboxyl activating agent is added last to a preformed mixture of the process components the amount of epimerization that occurs at the C-terminus amino acid of the oligopeptide moiety in the compound of formula Ia is less than when the base is added last to the reaction mixture.

In a more preferred further embodiment of the instant process, the oligopeptide of the formula A is mixed with the anthracycline antibiotic of the formula B in the presence of an additive and a base, and a carboxyl activating agent is thereafter added to the mixture in two or more portions.

In an embodiment of the instant invention, the anthracycline antibiotic is doxorubicin ($R^a$ is —$CH_2OH$, $R^b$ is —$OCH_3$, $R^c$ is H and $R^d$ is —OH).

In another embodiment of the instant invention, R is selected from:
a) acetyl; and
b)

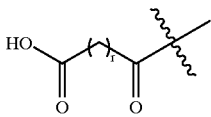

In another embodiment of the instant invention, R is

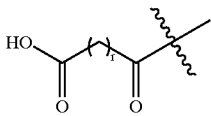

and R' is

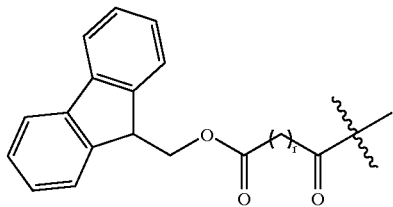

In another embodiment of the instant invention, R is

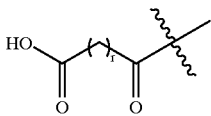

and R' is

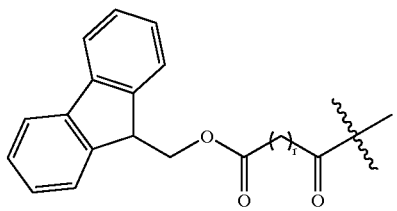

and the process further comprises the step of removing the protecting group by contacting the compound of formula Ia with piperidine.

In a preferred embodiment of the instant invention, the oligopeptide comprises an oligomer selected from:

a) 4-HypXaaSerTyrGln|SerSer (SEQ.ID.NO.: 1),
b) 4-HypXaaSerTyrGln|SerAla (SEQ.ID.NO.: 2),
c) Ala-4-HypXaaSerTyrTyr|Ser (SEQ.ID.NO.: 3),
d) AlaAsn4-HypXaaSerTyrGln|Ser (SEQ.ID.NO.: 4),
e) 4-HypXaaSerTyrGln|SerSerThr (SEQ.ID.NO.: 5),
f) 4-HypTyrGln|SerSerThr (SEQ.ID.NO.: 6),
g) 4-HypXaaSerTyrGln|SerSerSer (SEQ.ID.NO.: 7),
h) 4-HypTyrGln|SerSerSer (SEQ.ID.NO.: 8),
i) 4-HypXaaLysTyrGln|SerSerSer (SEQ.ID.NO.: 9),
j) 4-HypXaahArgTyrGln|SerSerSer (SEQ.ID.NO.: 10),
k) 4-HypXaaSerTyrGln|SerSerLeu (SEQ.ID.NO.: 11);
l) 4-HypTyrGln|SerSerLeu (SEQ.ID.NO.: 12);
m) 4-HypXaaSerTyrGln|SerLeu (SEQ.ID.NO.: 13);
n) 4-HypTyrGln|SerLeu (SEQ.ID.NO.: 14);
p) 4-HypXaaSerTyrGln|SerNle (SEQ.ID.NO.: 15);
q) 4-HypTyrGln|SerNle (SEQ.ID.NO.: 16);
r) 4-HypXaaSerTyrGln|SerTIC (SEQ.ID.NO.: 17);
s) 4-HypTyrGln|SerTIC (SEQ.ID.NO.: 18);
t) 4-HypXaaSerChgGln|SerLeu (SEQ.ID.NO.: 19);
u) 4-Hyp ChgGln|SerLeu (SEQ(ID.NO.: 20);
v) 4-HypXaaSerChgGln|SerNle (SEQ.ID.NO.: 21);
w) 4-HypChgGln|SerNle (SEQ.ID.NO.: 22);
x) 4-HypXaaSerChgGln|SerTIC (SEQ.ID.NO.: 23);
y) 4-HypChgGln|SerTIC (SEQ.ID.NO.: 24);
z) AlaSerTyrGln|SerSerLeu (SEQ.ID.NO.: 25);
aa) SerhArgChgGln|SerLeu (SEQ.ID.NO.: 26);
bb) hArgSerSerTyrGln|SerNle (SEQ.ID.NO.: 27);
cc) hArgAlaSerChgGln|SerLeu (SEQ.ID.NO.: 28);
dd) hArgSerSerTyrGln|SerLeu (SEQ.ID.NO.: 29);
ee) hArgSerSerChg|SerLeu (SEQ.ID.NO.: 30);
ff) SerhArgChgGln|SerLeu (SEQ.ID.NO.: 31);
gg) hArgTyrGln|SerLeu (SEQ.ID.NO.: 32);
hh) hArgSerSerChgGln|SerLeu (SEQ.ID.NO.: 33);
ii) SerhArgTyrGln|SerLeu (SEQ.ID.NO.: 34);
jj) SerSerTyrGln|SerLeu (SEQ.ID.NO.: 35);
kk) SerSerSerChgGln|SerLeu (SEQ.ID.NO.: 36);
ll) 3PAL-SerSerChgGln|SerLeu (SEQ.ID.NO.: 37);
mm) SerSerChgGln|SerLeu (SEQ.ID.NO.: 38);
nn) SerSerSerChgGln|Ser(dLeu) (SEQ.ID.NO.: 39);
oo) SerSerSerChgGln|SerVal (SEQ.ID.NO.: 40);
pp) ProSerSerChgGln|SerVal (SEQ.ID.NO.: 41);
qq) GlySerSerChgGln|SerLeu (SEQ.ID.NO.: 42);
rr) hSerSerSerChgGln|SerLeu (SEQ.ID.NO.: 43);
ss) hArgSerSerChgGln|SerNle (SEQ.ID.NO.: 44);
tt) hArgTyrGln|SerSerSerLeu (SEQ.ID.NO.: 45);
uu) LysTyrGln|SerSerSerLeu (SEQ.ID.NO.: 46);
vv) SerTyrGln|SerSerSerLeu (SEQ.ID.NO.: 47);
ww) SerSerChgGln-Ser(dLeu) (SEQ.ID.NO.: 48);
xx) 3PAL-SerSerChgGln-Ser(dLeu) (SEQ.ID.NO.: 49); and
yy) AlaSerChgGln-SerLeu (SEQ.ID.NO.: 50).

wherein 4-Hyp is 4-hydroxyproline, Xaa is any amino acid, hArg is homoarginine, hSer is homoserine, TIC is 1,2,3,4-tetrahydro-3-isoquinoline carboxylic acid, Cha is cyclohexylalanine and Chg is cyclohexylglycine.

Preferably Xaa in the more preferred embodiment is selected from Ala, Ser and Ile.

In a preferred embodiment the present invention is directed to a process for the preparation of the compound of formula 4:

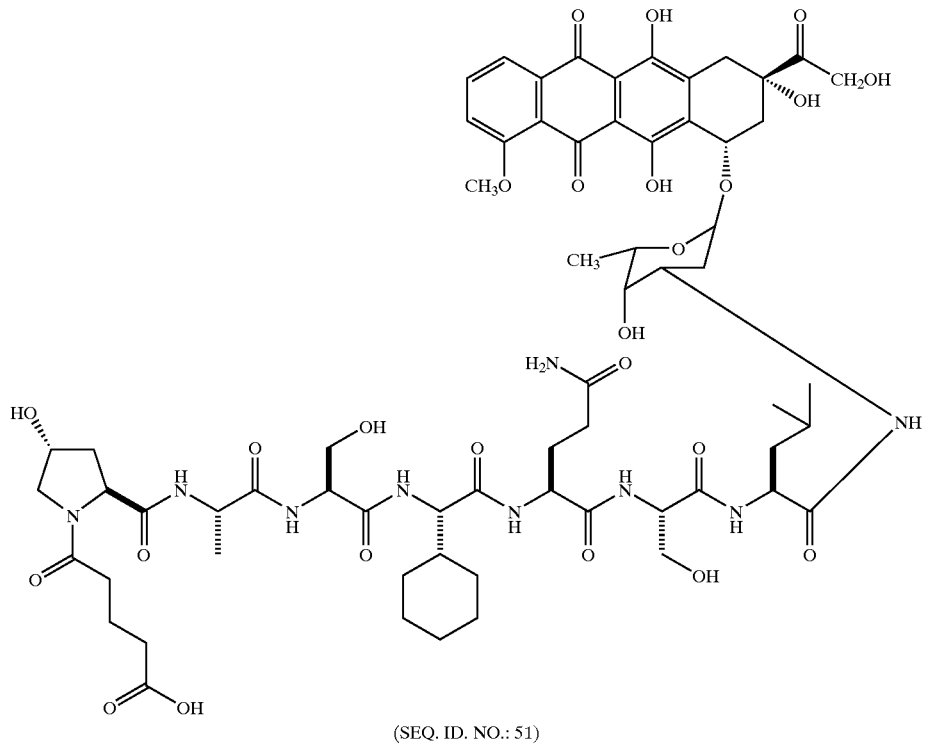
(SEQ. ID. NO.: 51)
or a pharmaceutically acceptable salt thereof;
which comprises the step of mixing an oligopeptide of the formula 2a:
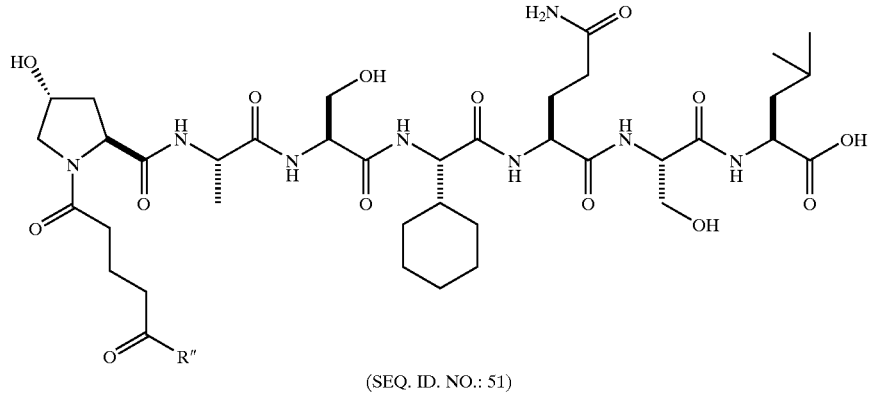
(SEQ. ID. NO.: 51)
wherein R″ is —OH or a protected precursor to —OH;
or a salt thereof;

with an anthracycline antibiotic of the formula 1:

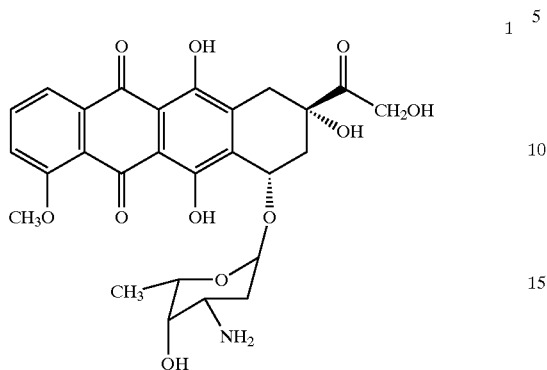

or a salt thereof;
in the presence of a carboxyl activating agent and, optionally, in the presence of a base, to form a compound of the formula 3a:

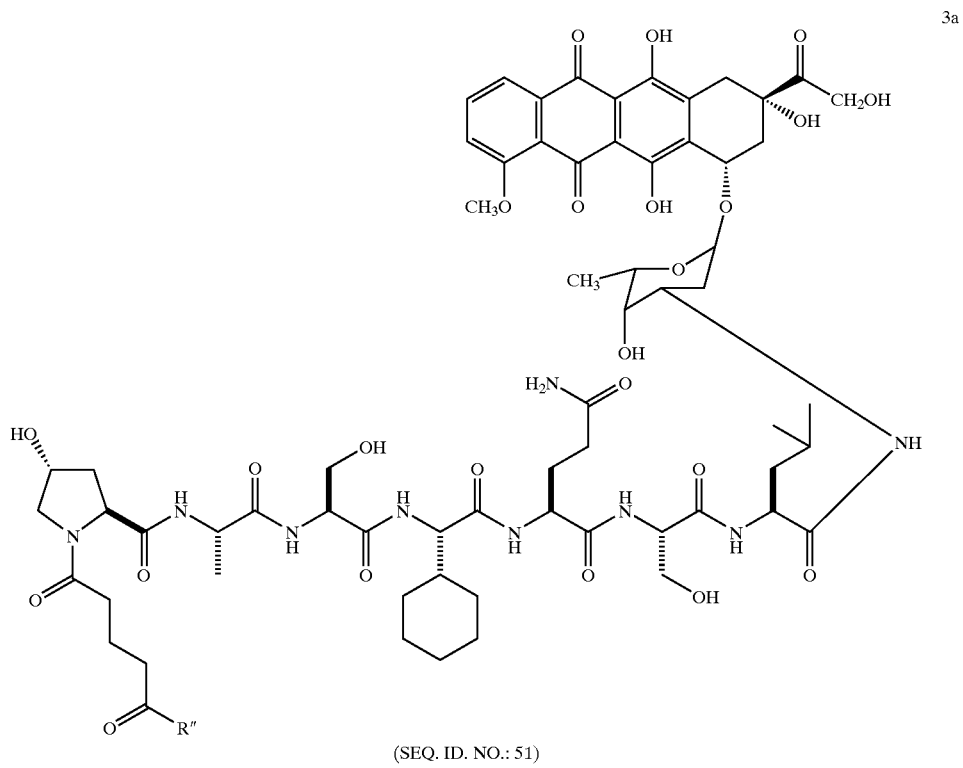

(SEQ. ID. NO.: 51)

or a salt thereof.

In a further embodiment of this preferred embodiment, the process further comprises the step of converting R″ to a —OH moiety.

In a more preferred embodiment, the present invention is directed to a process for the preparation of the compound of formula 4:

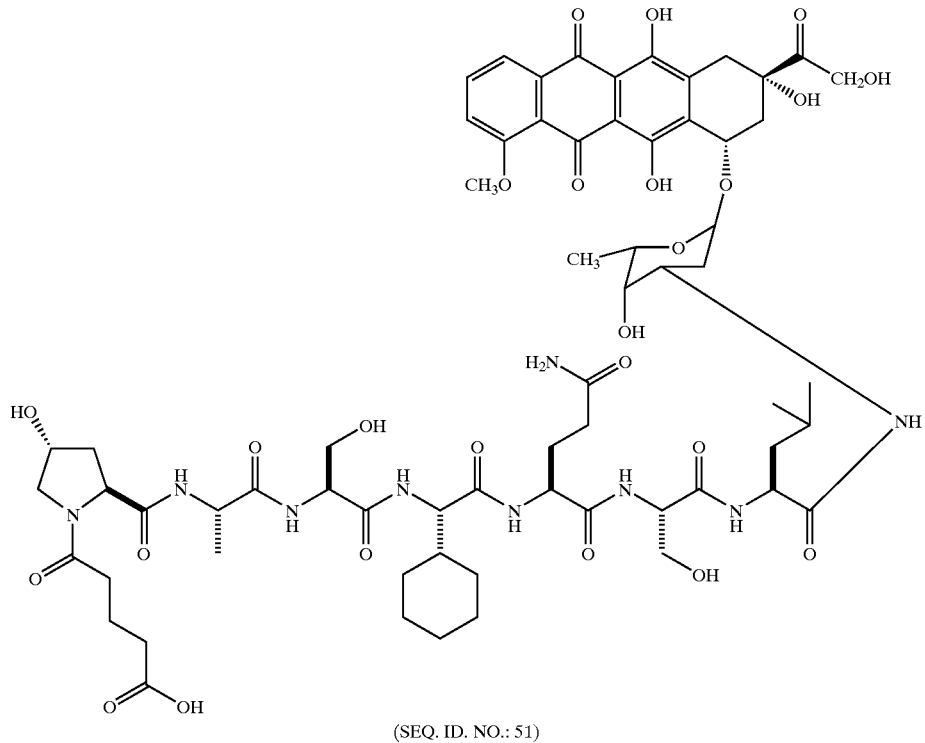
(SEQ. ID. NO.: 51)
or a pharmaceutically acceptable salt thereof;
which comprises the steps of:
a) mixing an oligopeptide of the formula 2:
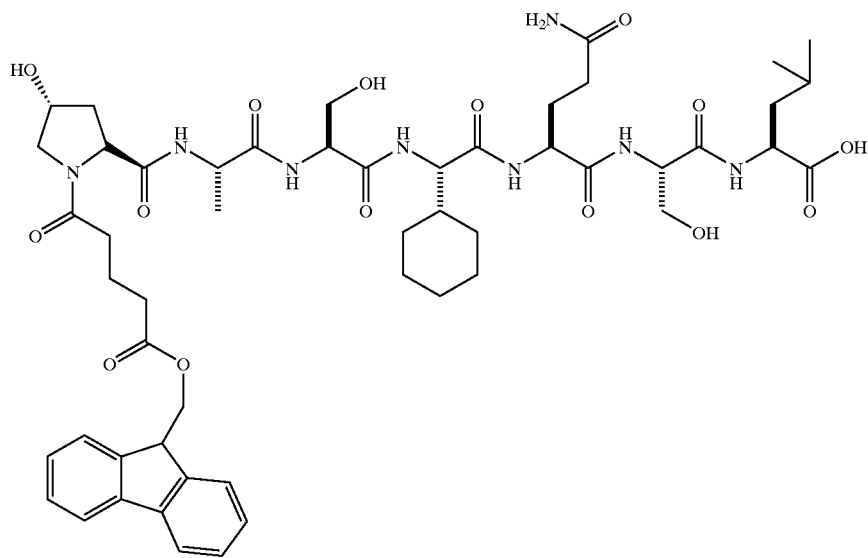
(SEQ. ID. NO.: 52)
or a salt thereof;

with an anthracycline antibiotic of the formula 1:

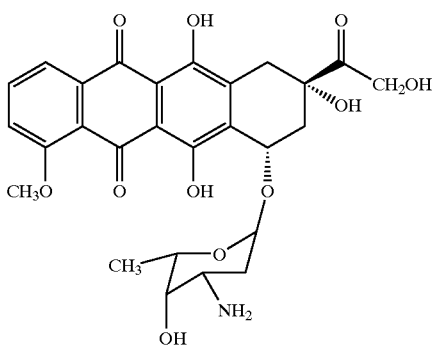

or a salt thereof;
in the presence of a carboxyl activating agent and, optionally, in the presence of a base, to form a compound of the formula 3:

1 is added to that slurry to form a second slurry. It has been surprisingly discovered that maintaining such a low temperature for addition of the oligopeptide to the reaction mixture and then adding the doxorubicin to the slurry at low temperature avoids the formation of a gel in the reaction mixture which is detrimental to a large scale preparation of the compound of the formula 3.

In a second further embodiment of the more preferred embodiment of the instant process, the anthracycline antibiotic of the formula 1 is mixed in a solvent, in particular DMF, optionally with an additive and optionally with a base, to form a first slurry, which is then cooled to about −6° C. to about −3° C. and the oligopeptide of the formula 2 is added to that slurry to form a second slurry.

In an embodiment of the further embodiments of the instant process, the oligopeptide of formula 1 is mixed with a salt of the anthracycline antibiotic of the formula 2 in the presence of a carboxyl activating agent and a base. Preferably, the salt of the anthracycline antibiotic of the formula 2 is the hydrochloride salt.

In an embodiment of the further embodiments of the instant process, the process further comprises the step of

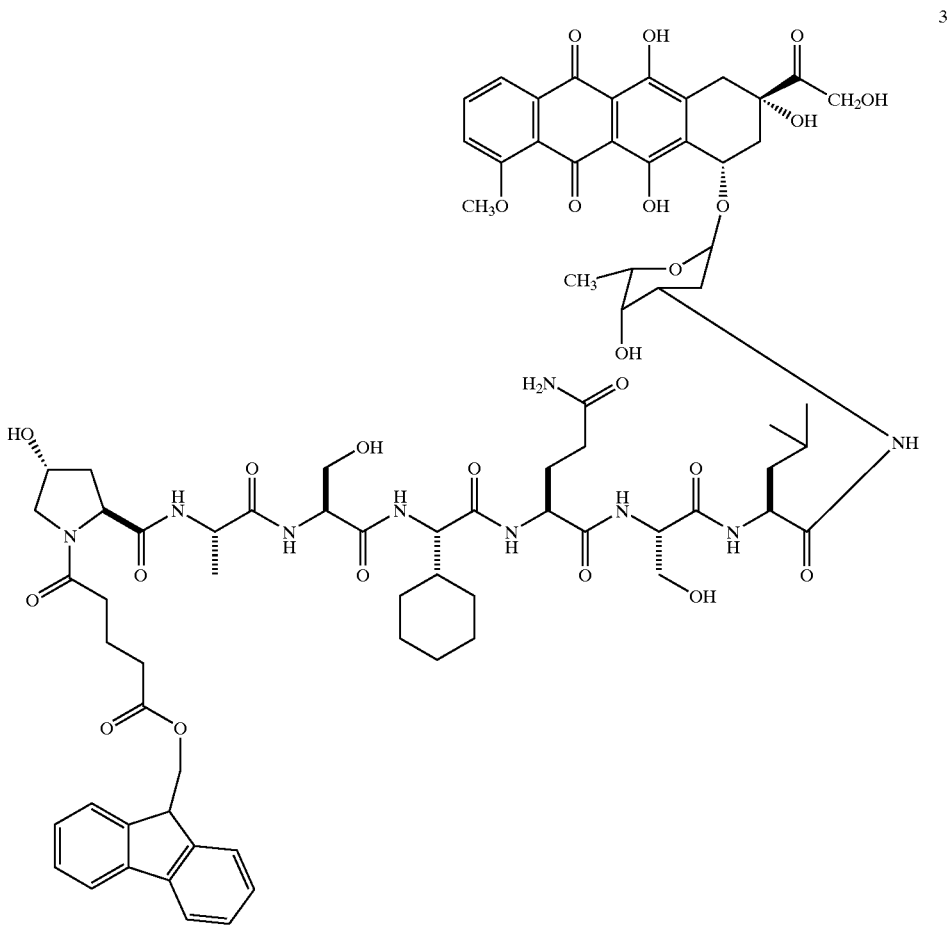

(SEQ. ID. NO.: 52)

or a salt thereof.

In a further embodiment of the more preferred embodiment of the instant process, the oligopeptide of the formula 2 is added to the reaction mixture that comprises a solvent, in particular DMF, at about −6° C. to about −3° C. to form a first slurry and the anthracycline antibiotic of the formula removing the fluorenylmethoxy protecting group of the compound of formula 3 to produce the compound of the formula 4.

In a further embodiment of the instant process, the step of removing the fluorenylmethoxy protecting group of the compound of formula 3 comprises contacting the compound of formula 3 with piperidine.

The phrase "oligomers that comprise an amino acid sequence" as used hereinabove, and elsewhere in the Detailed Description of the Invention, describes oligomers of from about 3 to about 100 amino acids residues which include in their amino acid sequence the specific amino acid sequence decribed and which are therefore proteolytically cleaved within the amino acid sequence described by free PSA. Preferably, the oligomer is from 5 to 10 amino acid residues. Thus, for example, the following oligomer:

hArgSer4-HypChgGln|SerLeu (SEQ.ID.NO.: 53); comprises the amino acid sequence:

4-HypChgGln|SerLeu (SEQ.ID.NO.: 54); and would therefore come within the instant invention.

The inclusion of the symbol "|" within an amino acid sequence indicates the point within that sequence where the oligopeptide is proteolytically cleaved by free PSA.

The compounds of the present invention may have asymmetric centers and occur as racemates, racemic mixtures, and as individual diastereomers, with all possible isomers, including optical isomers, being included in the present invention. Unless otherwise specified, named amino acids are understood to have the natural "L" stereoconfiguration. When any variable (e.g. aryl, heterocycle, $R^3$ etc.) occurs more than one time in any constituent, its definition on each occurence is independent of every other occurence. For example, $HO(CR^1R^2)_2$— represents $HOCH_2CH_2$—, $HOCH_2CH(OH)$—, $HOCH(CH_3)CH(OH)$—, etc. Also, combinations of substituents and/or variables are permissible only if such combinations result in stable compounds.

The following abbreviations are utilized in the specification and tables to denote the indicated amino acids and moieties:

| | |
|---|---|
| hR or hArg: | homoarginine |
| hY or hTyr: | homotyrosine |
| Cha: | cyclohexylalanine |
| Amf: | 4-aminomethylphenylalanine |
| DPL: | 2-(4,6-dimethylpyrimidinyl)lysine |
| (imidazolyl)K: | $N^t$-(2-imidazolyl)lysine |
| $Me_2PO_3$-Y: | O-dimethylphosphotyrosine |
| O-Me-Y: | O-methyltyrosine |
| TIC: | 1,2,3,4-tetrahydro-3-isoquinoline carboxylic acid |
| DAP: | 1,3-diaminopropane |
| TFA: | trifluoroacetic acid |
| AA: | acetic acid |
| 3PAL | 3-pyridyl-alanine |
| 4-Hyp | 4-hydroxyproline |
| Abu | alpha-aminobutyric acid |
| Thi | thienylalanine |
| Boc/BOC | t-Butoxycarbonyl; |
| DMAc | dimethylacetamide |
| DMF | Dimethylformamide; |
| DMSO | Methyl sulfoxide; |
| EDC | 1-(3-dimethylaminopropyl)-3-ethyl-carbodiimide; |
| EtOAc | Ethyl acetate; |
| EtOH | Ethanol; |
| FAB | Fast atom bombardment; |
| HOAt | 1-Hydroxy-7-azabenzotriazole |
| HOBt | 1-Hydroxybenzotriazole hydrate; |
| HOPO | 2-hydroxypyridine-N-oxide |
| HPLC | High-performance liquid chromatography; |
| IPAc | isopropylacetate |
| MeOH | methanol |
| RPLC | Reverse Phase Liquid Chromatography |
| TFA | Trifluoroacetic acid; |
| THF | Tetrahydrofuran. |

As used herein, "alkyl" and the alkyl portion of aralkyl and similar terms, is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

"Alkynyl" groups include those groups having the specified number of carbon atoms and having one triple bonds. Examples of alkynyl groups include acetylene, 2-butynyl, 2-pentynyl, 3-pentynyl and the like.

"Halogen" or "halo" as used herein means fluoro, chloro, bromo and iodo.

As used herein, "aryl," and the aryl portion of aralkyl and aroyl, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyt, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein in the terms "substituted $C_{1-8}$ alkyl", "substituted aryl" and "substituted heterocycle" include moieties containing from 1 to 3 substituents in addition to the point of attachment to the rest of the compound. Such additional substituents are selected from F, Cl, Br, $CF_3$, $NH_2$, $N(C_1-C_6$ alkyl$)_2$, $NO_2$, CN, $(C_1-C_6$ alkyl)O—, —OH, $(C_1-C_6$ alkyl)S(O)$_m$—, $(C_1-C_6$ alkyl)C(O)NH—, $H_2N$—C (NH)—, $(C_1-C_6$ alkyl)C(O)—, $(C_1-C_6$ alkyl)OC(O)—, $N_3$, $(C_1-C_6$ alkyl)OC(O)NH— and $C_1-C_{20}$ alkyl.

The term "an integer between 1 and 10" represents the numbers 1 and 10 as well as those integers between those numbers. The term "an integer between 1 and 100" represents the numbers 1 and 100 as well as those integers between those numbers.

When $R^1$ and $R^2$ are combined to form —$(CH_2)_s$—, the cyclic moieties and heteroatom-containing cyclic moieties so defined include, but are not limited to:

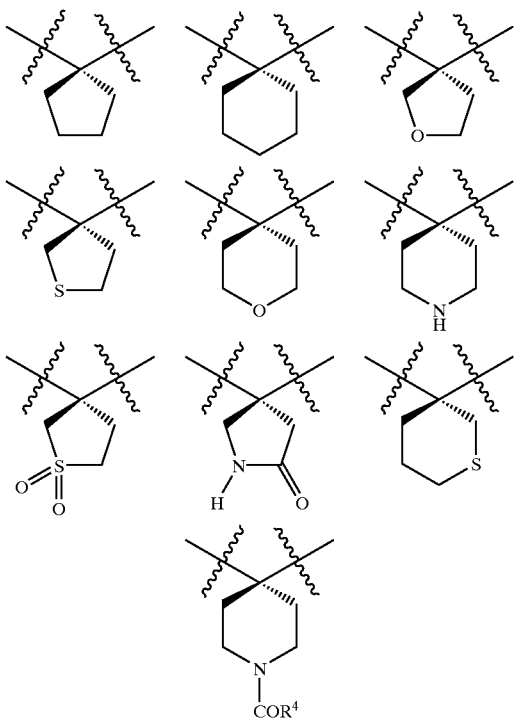

As used herein, the term "PEG" represents certain polyethylene glycol containing substituents having the designated number of ethyleneoxy subunits. Thus the term PEG(2) represents

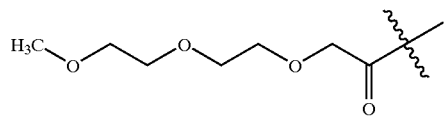

and the term PEG(6) represents

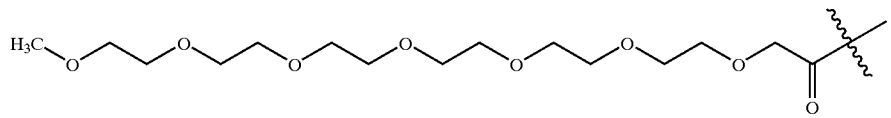

As used herein, the term "(2R)(2,3-dihydroxypropionyl)" represents the following structure:

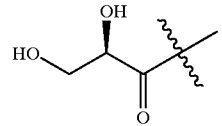

As used herein, the term "(2R,3S) 2,3,4-trihydroxybutanoyl" represents the following structure:

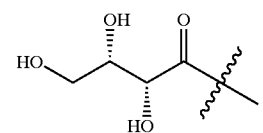

The following compounds are specific examples of a oligopeptide-cytotoxic agent conjugate that may be prepared by the process of the instant invention:

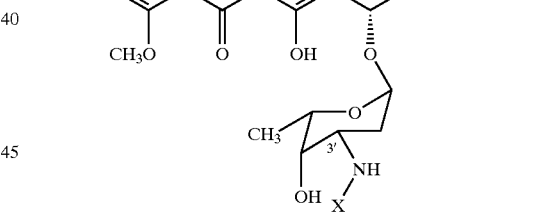

wherein X is:

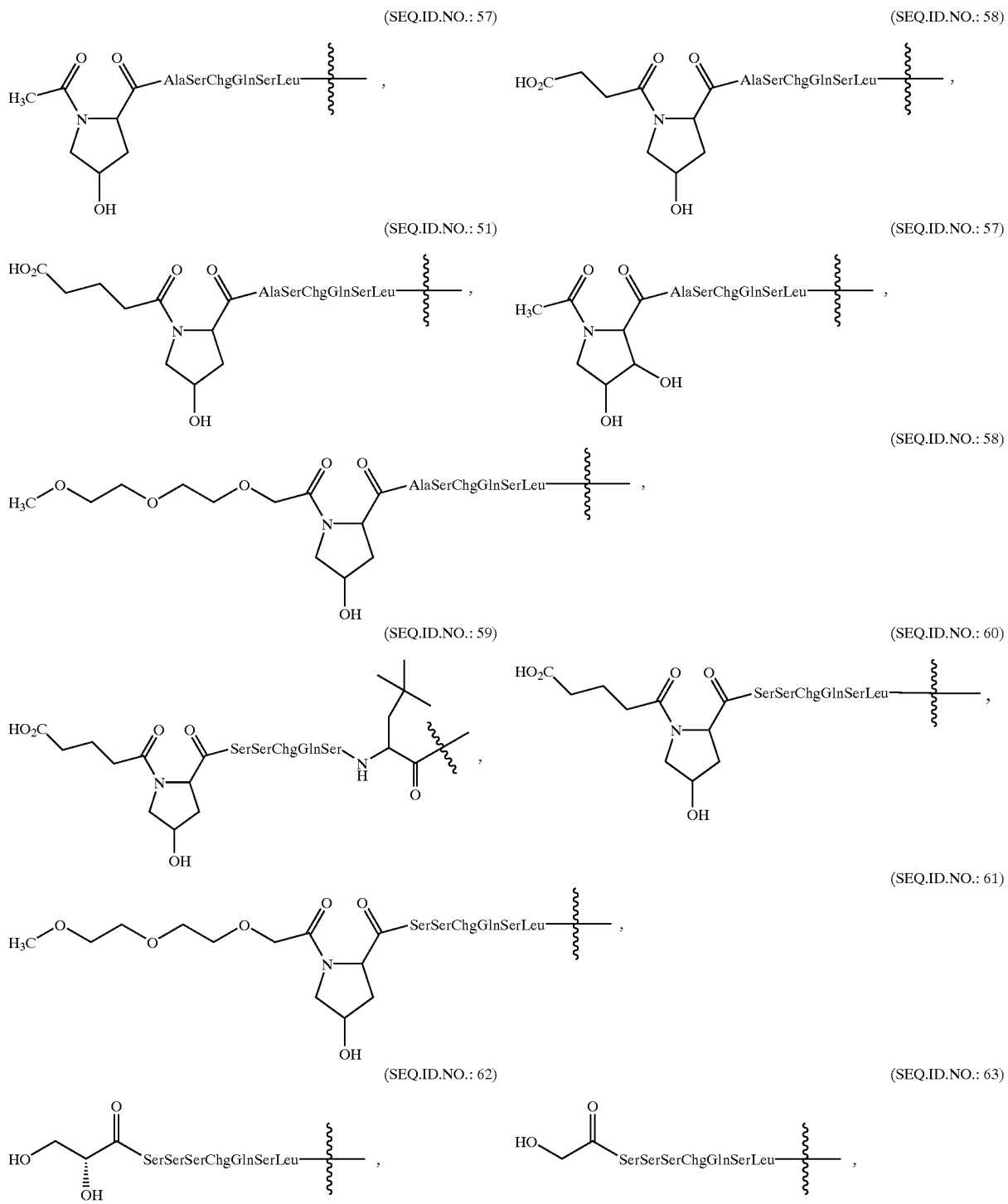

or an optical isomer or pharmaceutically acceptable salt thereof.

Other PSA conjugate compounds that may be prepared by the process of the instant invention include, but are not limited to, the compounds described in the following patents and patent publications:

U.S. Pat. No. 5,599,686, issued Feb. 4, 1997;
U.S. Pat. No. 5,866,679, issued Feb. 2, 1999;
WO 96/00503 (Jan. 11, 1996); U.S. Ser. No. 08/468,161 filed on Jun. 6, 1997 now U.S. Pat. No. 6,143,864;
WO 98/10651 (Mar. 19, 1998); U.S. Ser. No. 08/926,412 filed on Sep. 9, 1997 now U.S. Pat. No. 5,978,362; and
U.S. Pat. No. 5,948,750, issued Sep. 7, 1999; WO 98/18493 (May 7, 1998);
U.S. Ser. No. 08/950,805, filed on Oct. 14, 1997, now U.S. Pat. No. 5,948,750.

The pharmaceutically acceptable salts of the conjugates that may be prepared by the process of this invention and salts of Compounds of the formulae A, B, 1, 2a and 3a utilized in the instant processes include the conventional non-toxic salts of the compounds, e.g., non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like.

With respect to the conjugates described herein which comprise a N-terminus blocking group on the peptide which contains a carboxylic acid moiety, a pharmaceutically acceptable salt may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium and the like.

For the purpose of the process of the instant invention, the carboxyl activating agent may be selected from the group including, but not limited to, 2-(1H-benzotriazol-1-yl)-1,1, 3,3-tetramethyluronium hexafluorophosphate (known as HBTU), 1-hydroxybenzotriazole hydrate (known as HOBt), dicyclohexylcarbodiimide (DCC), N-ethyl-N-(3-dimethylaminopropyl)-carbodiimide (EDC), diphenylphosphorylazide (DPPA), benzotriazol-1-yl-oxy-tris-(dimethylamino)phosphonium hexafluorophosphate (BOP), 1,3-diisopropylcarbodiimide (DIC) and the like, used in combination or singularly. Preferably the carboxyl activating agent is selected from EDC, DIC and DCC. Most preferably the carboxyl activating agent is EDC.

The coupling reaction of the amine moiety to the carboxyl terminus may also comprise a base, such as 2,4,6-collidine, lutidine, pyridine, triethyl amine, Hünig's base ((iPr)$_2$NEt) and the like. Preferably the base is selected from 2,4,6-collidine and lutidine. Most preferably the base is 2,4,6-collidine. The coupling reaction may also comprise an additive, such as 1-hydroxy-7-azabenzotriazole (HOAt), 1-hydroxybenzotriazole (HOBt), 2-hydroxypyridine-N-oxide, (HOPO), N-hydroxysuccinimide, pyridine N-oxide and the like, or combinations thereof Preferably the additive is selected from HOAt, HOPO, HOBt or combinations thereof. More preferably the additive is HOAt. Also, more preferable the additive is a combination of HOPO and HOAt. The coupling reaction may also comprise a solvent. Such a solvent may be selected from N,N-dimethylformamide (DMF), N,N-dimethylacetamide (DMAc), N-methylpiperidone (NMP), aqueous THF, and the like. Preferably the solvent is selected from a polar aprotic organic solvent, such as DMF, DMAc, NMP and the like. Most preferably, the solvent is DMF.

One skilled in the art understands that in the synthesis of compounds of the invention, one may need to protect various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to *Protective Groups in Organic Chemistry*, McOmie, ed., Plenum Press, N.Y., N.Y. (1973); and, *Protective Groups in Organic Synthesis*, Greene, ed., John Wiley & Sons, N.Y., N.Y. (1981) for the teaching of protective groups which may be useful in the preparation of compounds of the present invention.

By way of example only, useful amino-protecting groups may include, for example, $C_1$–$C_{10}$ alkanoyl groups such as formyl, acetyl, dichloroacetyl, propionyl, hexanoyl, 3,3-diethylhexanoyl, γ-chlorobutryl, and the like; $C_1$–$C_{10}$ alkoxycarbonyl and $C_5$–$C_{15}$ aryloxycarbonyl groups such as tert-butoxycarbonyl, benzyloxycarbonyl, allyloxycarbonyl, 4-nitrobenzyloxycarbonyl, fluorenylmethyloxycarbonyl and cinnamoyloxycarbonyl; halo-($C_1$–$C_{10}$) alkoxycarbonyl such as 2,2,2-trichloroethoxycarbonyl; and $C_1$–$C_{15}$ arylalkyl and alkenyl group such as benzyl, phenethyl, allyl, trityl, and the like. Other commonly used amino-protecting groups are those in the form of enamines prepared with β-keto-esters such as methyl or ethyl acetoacetate.

Useful carboxy-protecting groups may include, for example, $C_1$–$C_{10}$ alkyl groups such as methyl, tert-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri-($C_1$–$C_3$ alkyl)silyl, such as trimethylsilyl, β-p-toluenesulfonylethyl, β-p-nitrophenylthio-ethyl, 2,4,6-trimethylbenzyl, β-methylthioethyl, phthalimidomethyl, 2,4-dinitrophenylsulphenyl, 2-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

With respect to the preferred embodiment of an oligopeptide combined with the anthracycline antibiotic doxorubicin, the following Reaction Schemes illustrate the synthesis of the conjugates of the instant invention. Other bases than piperidine are useful in the deprotection illustrated in Reaction Scheme IV, including dimethyl amine, diethyl, amine, pyrrolidine, quinuclidine and the like. Preferably piperidine is utilized.

REACTION SCHEME I

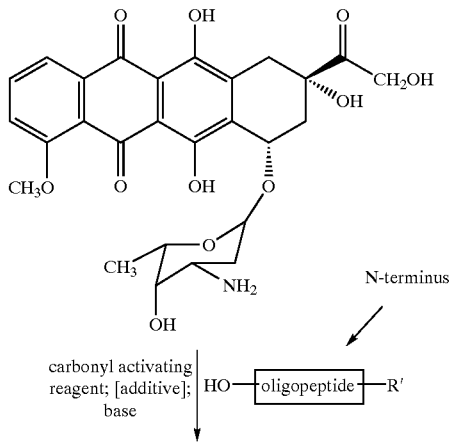

-continued
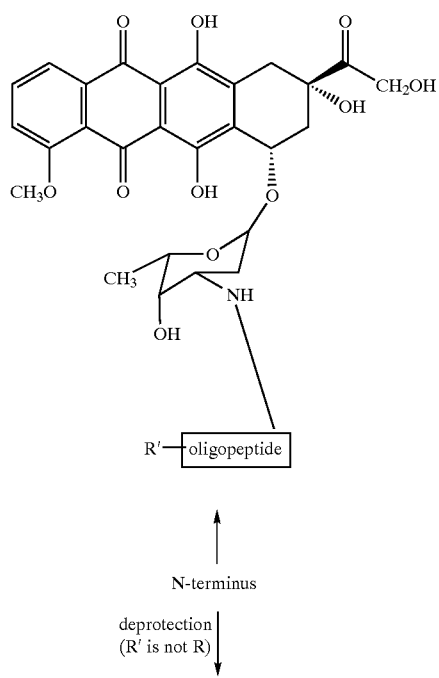
↑ N-terminus
deprotection
(R' is not R) ↓
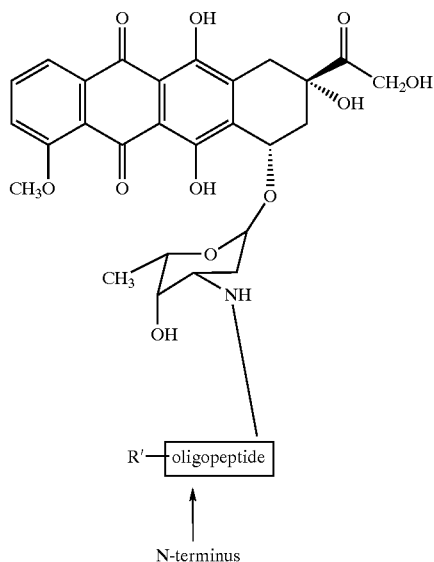
↑ N-terminus
REACTION SCHEME II
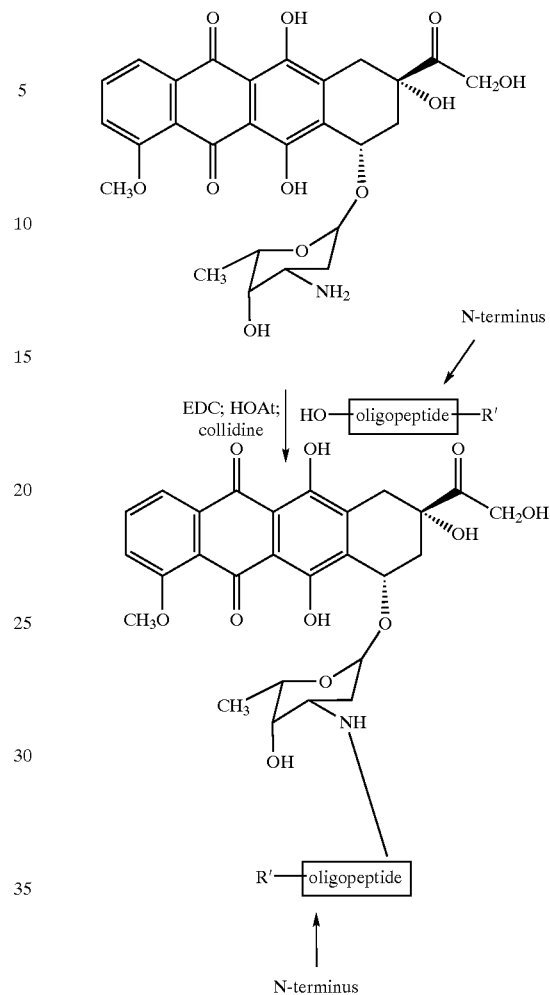
REACTION SCHEME III
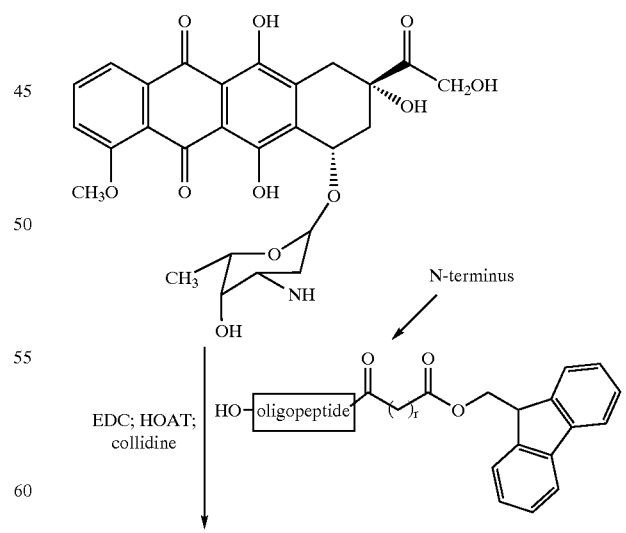

25
-continued
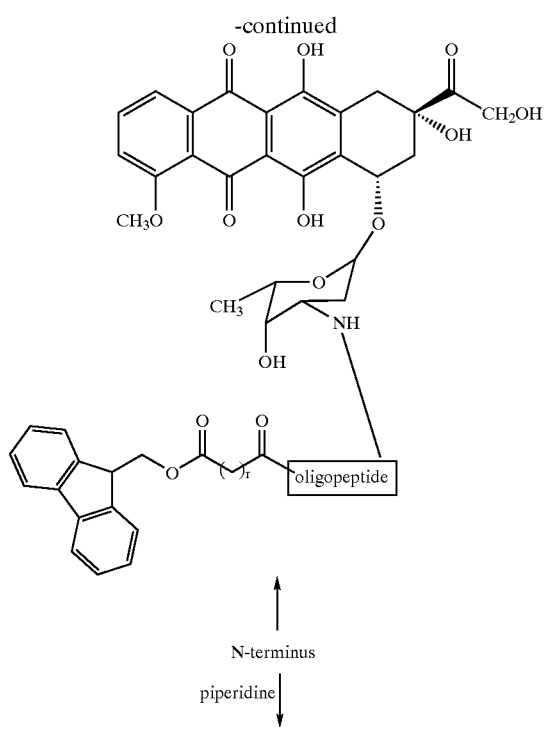
26
-continued
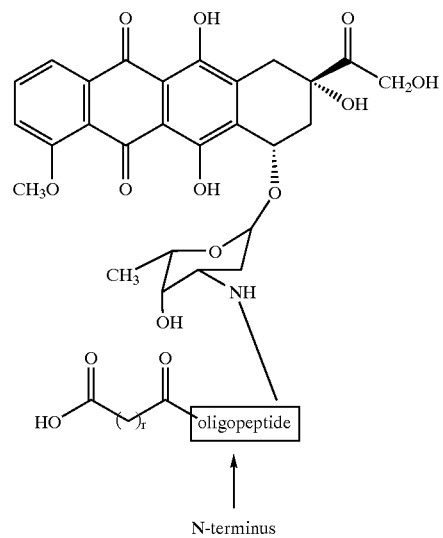
REACTION SCHEME IV
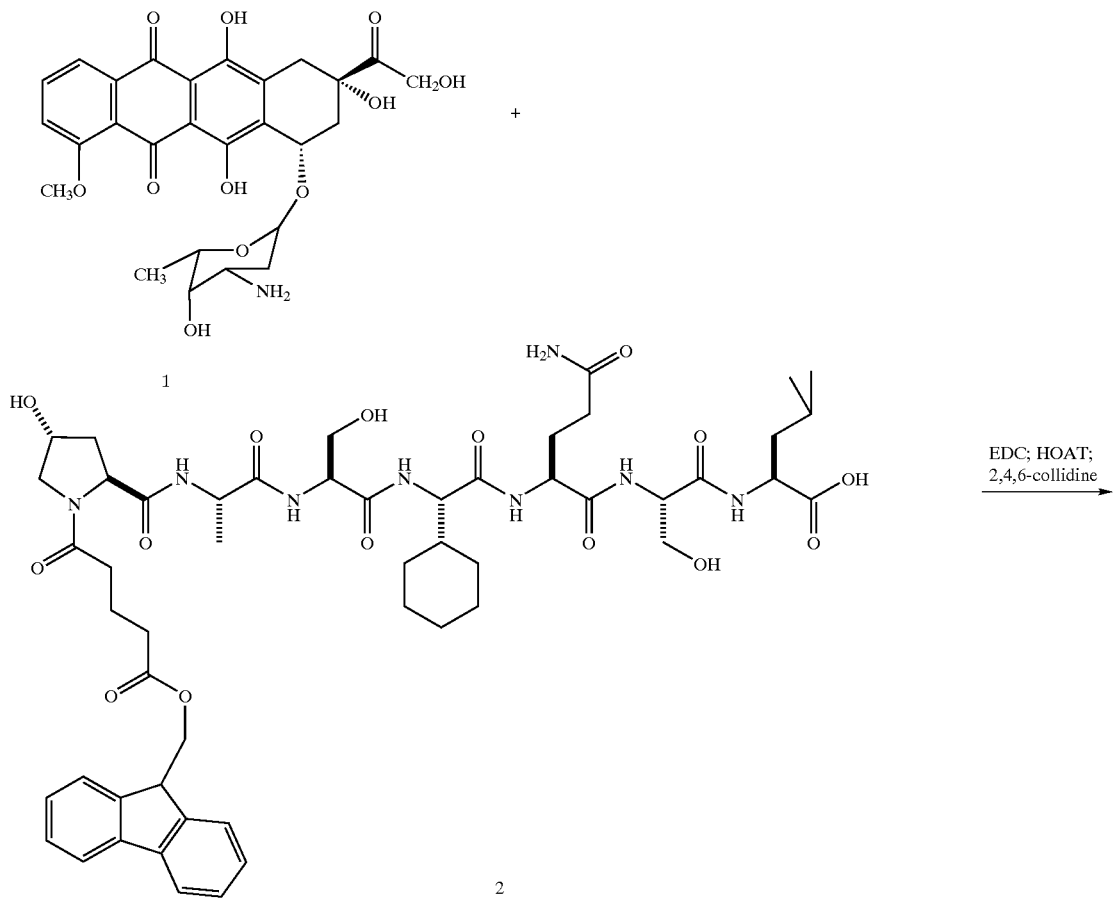
(SEQ.ID.NO.: 52)

-continued
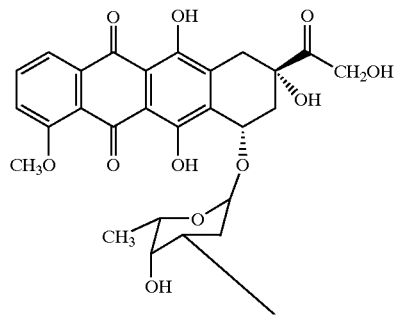
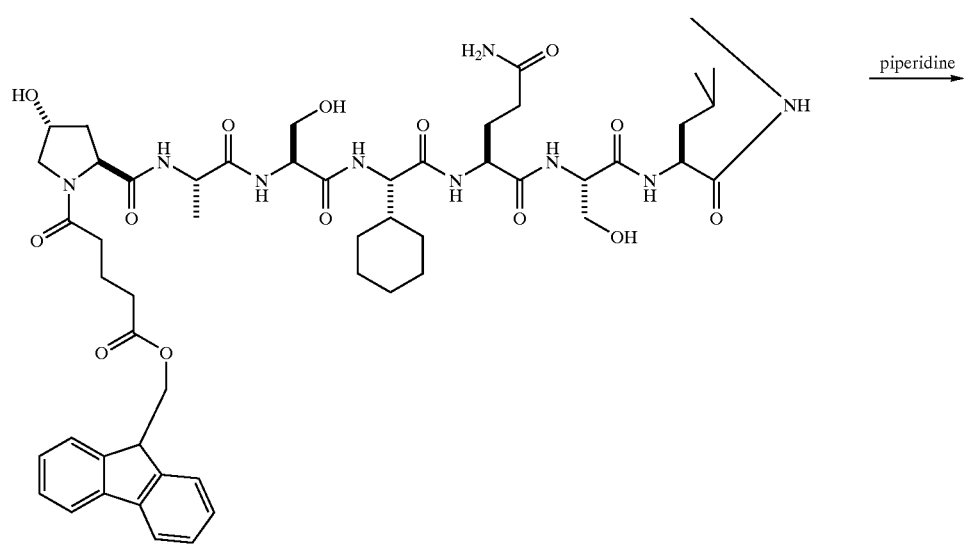
3
(SEQ.ID.NO.: 52)
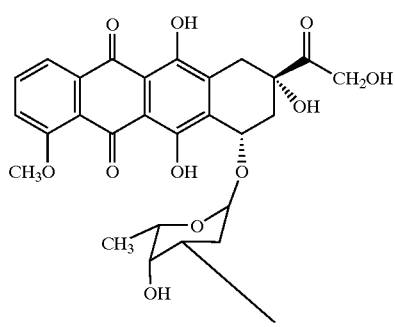

-continued

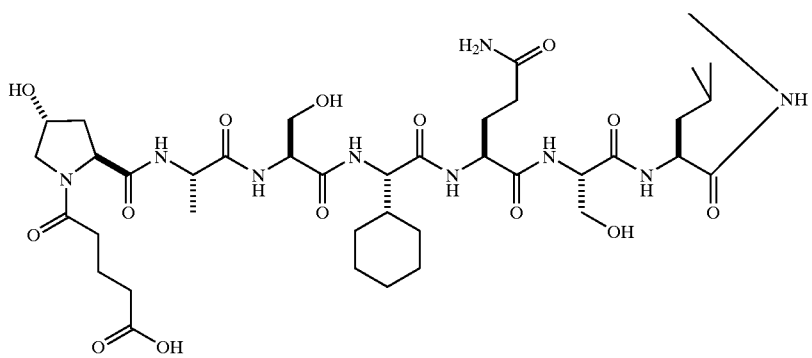

4
(SEQ.ID.NO.: 51)

Reaction Schemes V–VIII below illustrate other methods for the preparation of the PSA conjugates, in particular, the preparation of the compound of formula 4. Thus, as shown in Reaction Scheme V, an unblocked glutaryl peptide 5 may be prepared by methods well known in the art and coupled to the amine moiety of the anthracycline cytotoxic agent as described above. Specific preparation of the compound of formula 4 is illustrated in Reaction Scheme VI.

Alternatively, as illustrated in Reaction Scheme VII, a bis-blocked peptide 6 may be prepared by methods well known in the art and selectively deprotected to provide the benzyl ester analog of the compound of formula 2. After coupling to the anthracycline cytotoxic agent as described above, deprotection of the acid moiety can be accomplished by catalytic hydrogenation, thereby avoiding prolonged exposure of compound 4 to a base. Other carboxylic acid protecting groups that may be useful include t-butyl, sillyl and the like. It is known that the anthracyclines are chemically sensitive to base.

In yet another embodiment, the cleavable peptide portion of the instant conjugate may be attached in two or more fragments, as ilustrated in Reaction Scheme VIII. Such a synthetic strategy might allow more flexibility in selection and use of blocking groups. The particular selection of which peptide fragment to attach first that is shown in the scheme is illustrative only and is not meant to limiting.

REACTION SCHEME V

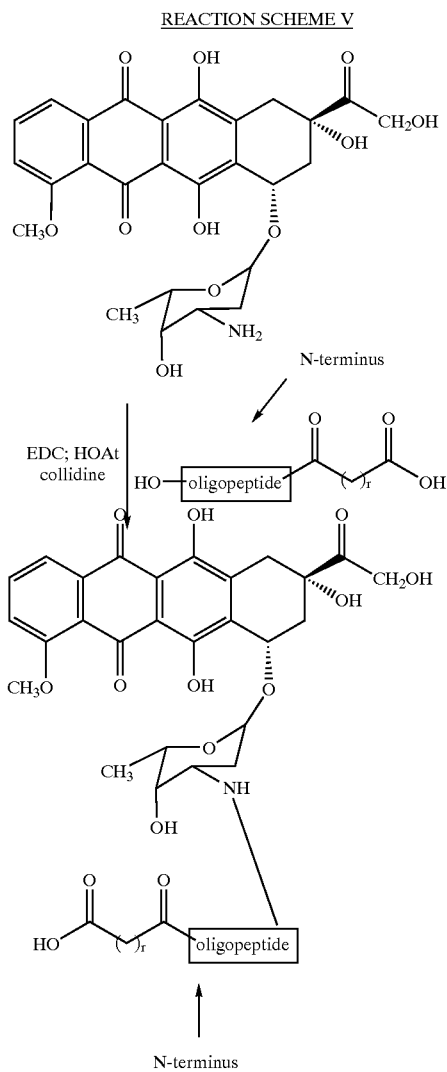

REACTION SCHEME VI
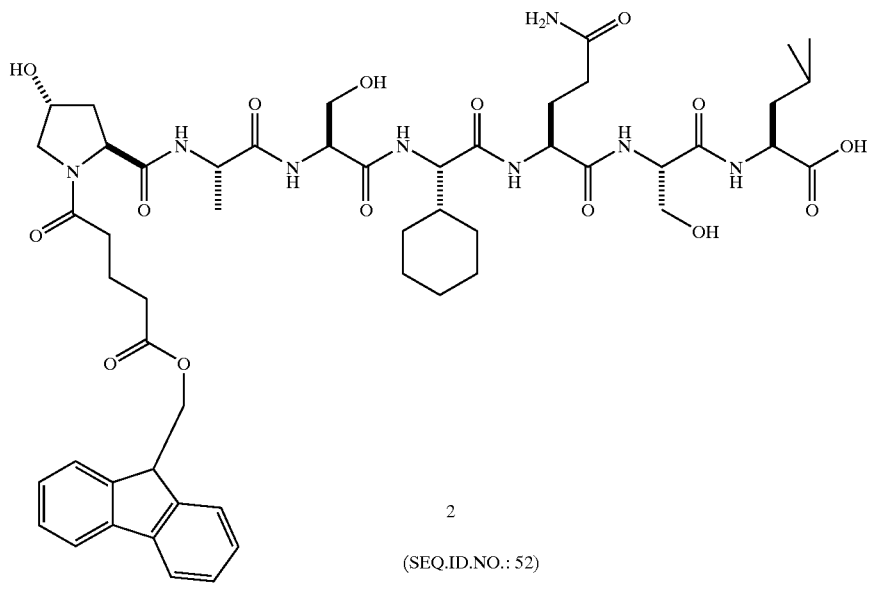
2
(SEQ.ID.NO.: 52)
↓ quinuclidine
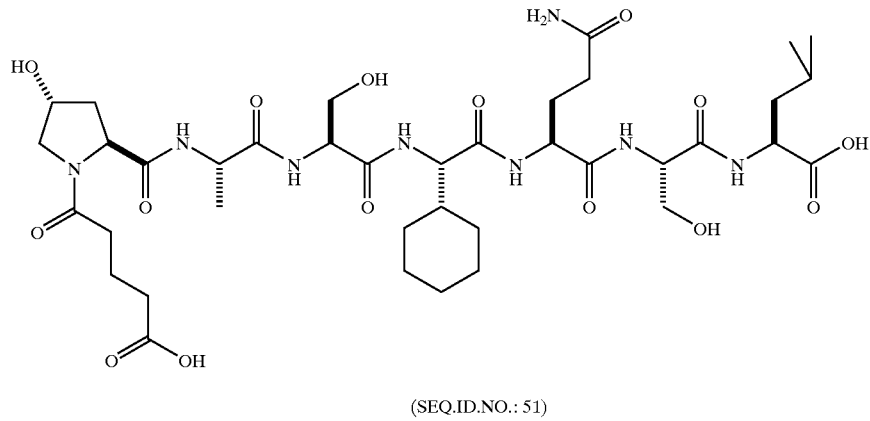
(SEQ.ID.NO.: 51)
↓ 1; EDC, 2, 4, 6-collidine
   HOAt
4

REACTION SCHEME VII
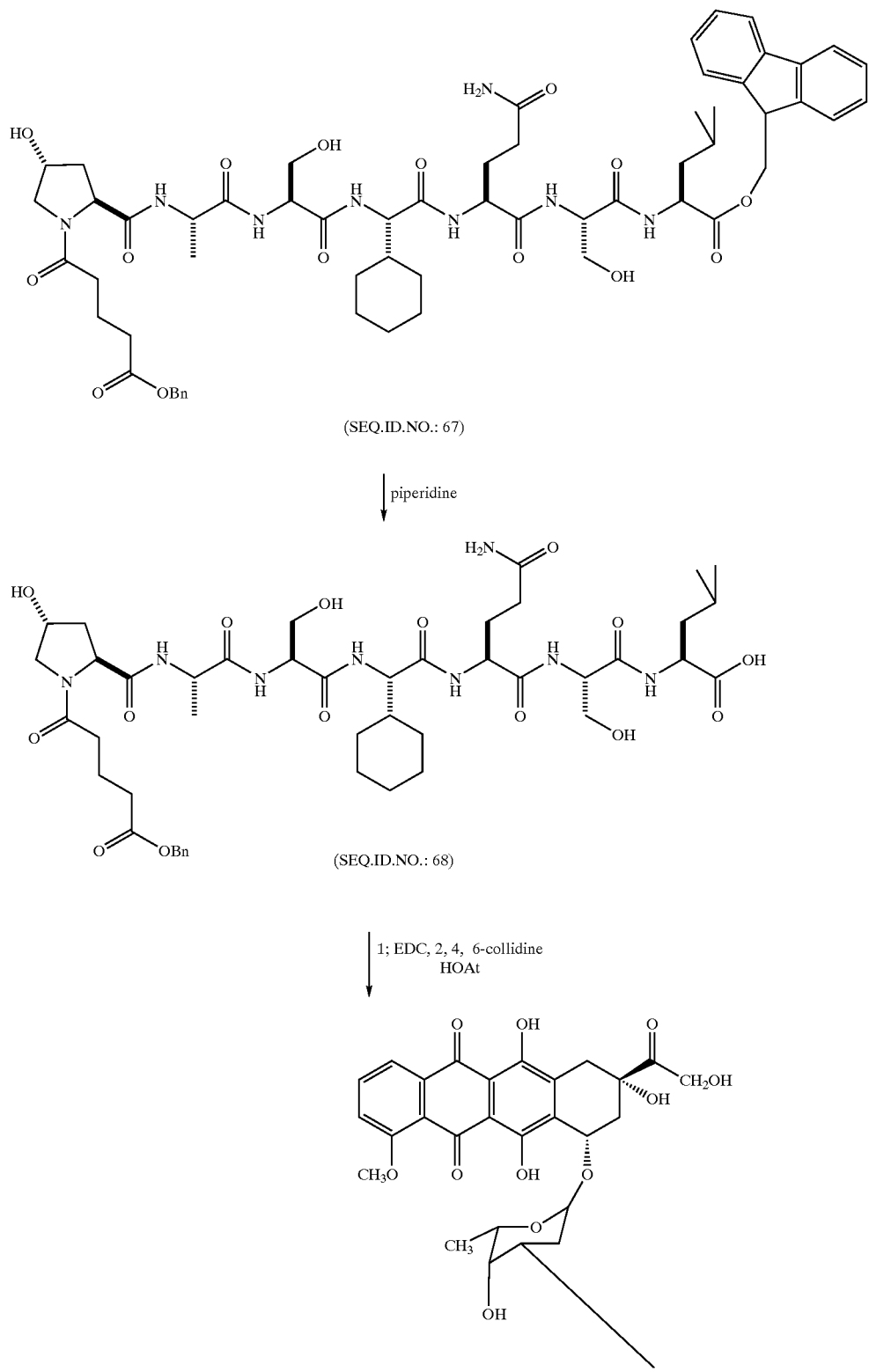
(SEQ.ID.NO.: 67)
↓ piperidine
(SEQ.ID.NO.: 68)
↓ 1; EDC, 2, 4, 6-collidine
   HOAt -continued
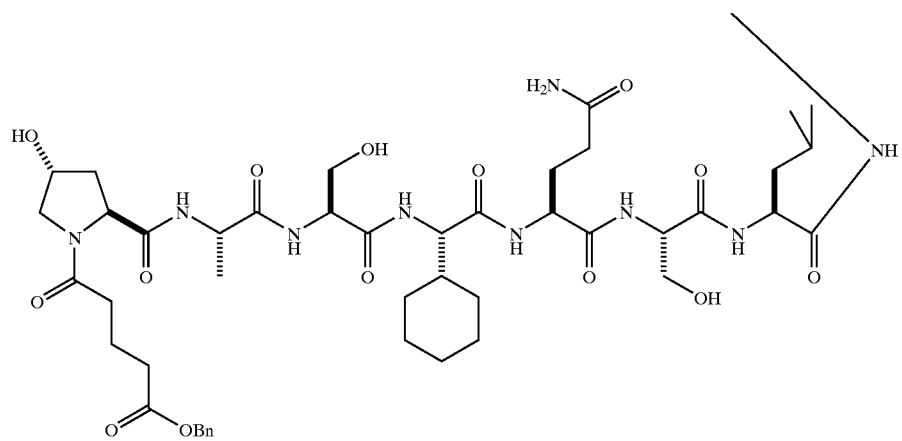
(SEQ.ID.NO.: 68)
↓ H₂, Pd/C
4
REACTION SCHEME VIII
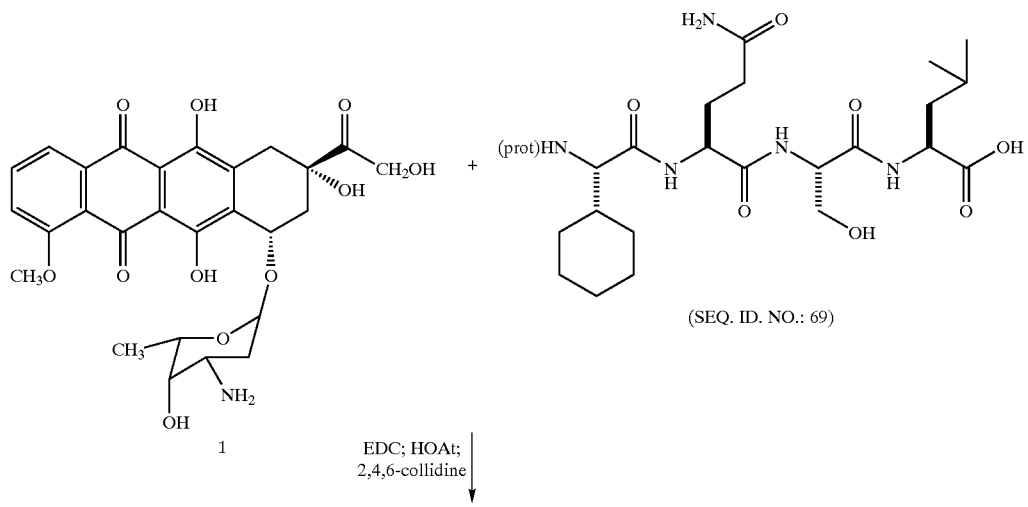
(SEQ. ID. NO.: 69)
EDC; HOAt; 2,4,6-collidine ↓

-continued
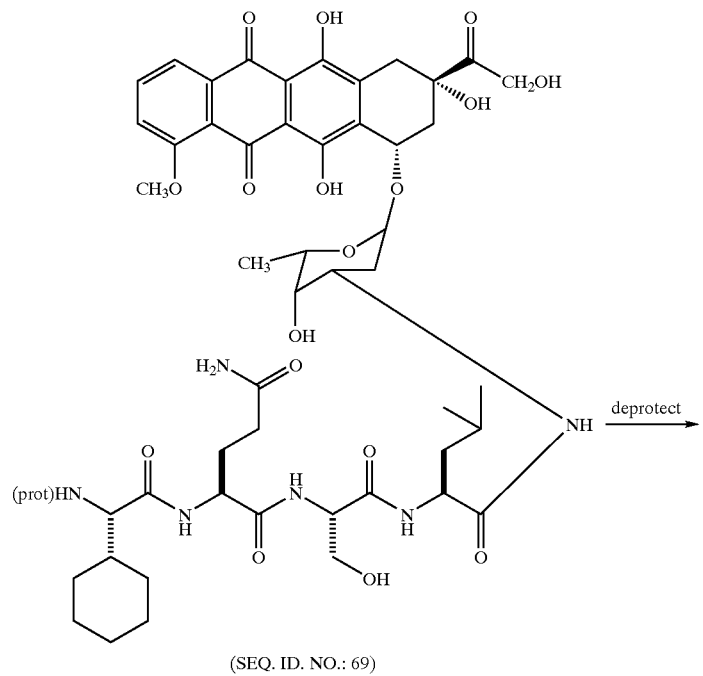
(SEQ. ID. NO.: 69) →deprotect
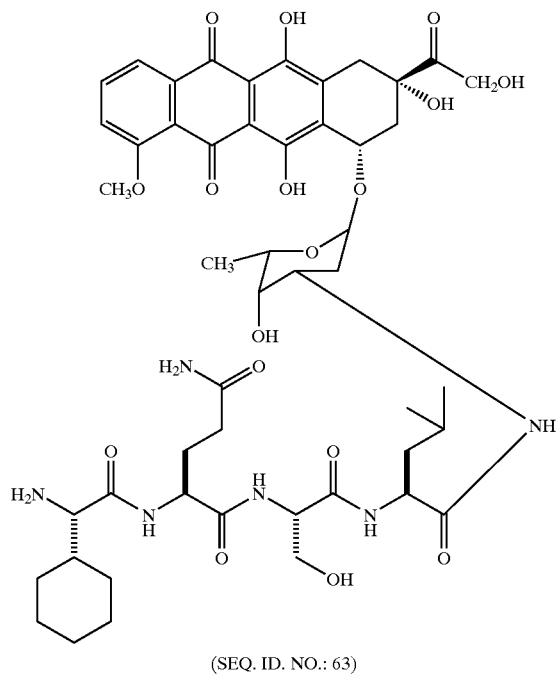
(SEQ. ID. NO.: 63)

-continued

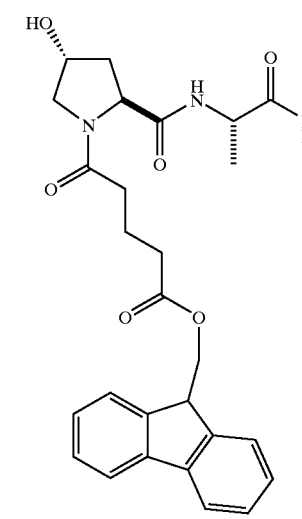

EDC; HOAt;
collidine

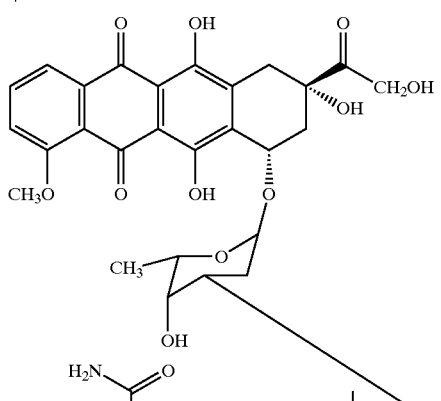

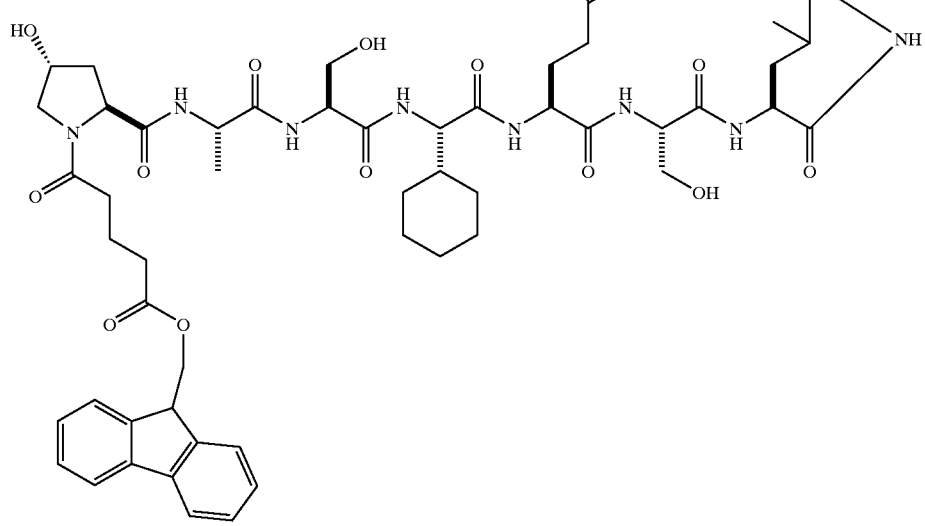

3
(SEQ. ID. NO.: 52)

piperidine

4

One skilled in the art will appreciate that although specific reagents and reaction conditions are outlined in the following examples, modification can be made which are meant to be encompassed by the spirit and scope of the invention. The following preparations and examples, therefore, are provided to further illustrate the invention, and are not limiting.

Unless otherwise indicated, all amino acids described in the examples have the natural (L) stereoconfiguration.

EXAMPLE 1

Preparation N-(N'-(Fm-Glutaryl)-trans-4-hydroxy-L-prolinyl-alanyl)serine

Step 1: N-Boc-trans-4-hydroxy-L-proline

A solution of trans-4-hydroxy-L-proline (3.0 kg, 22.88 M) in 1 M aqueous sodium hydroxide (25.2 L) and tert-butanol (12.0 L) was treated with a solution of di-tert-butyldicarbonate (5.09 kg) in tert-butanol (6.0 L) at 20° C. over 20 minutes. Upon complete addition, the resulting solution was stirred at 20° C. for 2 hours. The solution was extracted with hexane (2×15.0 L) and then acidified to pH 1 to 1.5 by cautious addition of a solution of potassium hydrogen sulphate (3.6 kg) in water (15.0 L). The mixture was extracted with ethyl acetate (3×15.0 L). The combined ethyl acetate extracts were washed with water (2×1.0 L) and dried by azeotropic distillation at atmospheric pressure (final KF of ethyl acetate solution <0.1%).

The ethyl acetate solution was then concentrated by atmospheric distillation to a volume of 15.0 L, diluted with hexane (8.0 L), seeded and stirred at 20° C. for 1 hour. Hexane (22.5 L) was added over 2 hours, the slurry was cooled to 0° C. for 1 hour and the solid collected by filtration. The product was washed with cold (0° C.) 2:1 hexane/ethyl acetate (15.0 L) and dried in vacuo at 45° C. to afford the title compound as a white crystalline solid.

Step 2: N-Boc-trans-4-hydroxy-L-proline Pentafluorophenyl ester

Boc-trans-4-hydroxy-L-proline (3.5 kg) (prepared as described in Step 1) and pentafluorophenol (3.06 kg) were dissolved in ethyl acetate (52 L). The solution was treated with a solution of dicyclohexylcarbodiimide (3.43 kg) in ethyl acetate (8 L) and the mixture was stirred at room temperature for 2 hours. The resulting slurry was cooled to 0° C., filtered and the solids washed with ethyl acetate (15 L). The filtrate was evaporated at atmospheric pressure to a volume of 10 L and diluted with hexane (100 L). The resulting mixture was stirred at room temperature overnight and then cooled to 0° C. for 1 hour. The solid was collected by filtration, washed with cold (° C.) 10:1 hexane/ethyl acetate (15 L) and dried at 45° C. in vacuo to afford the title compound as a white crystalline solid.

Step 3: N-(trans-4-Hydroxy-L-prolinyl-alanyl)serine Hydrochloride

N-alanylserine (1.5 kg, 8.515 M) and Boc-trans-4-hydroxy-L-proline (3.72 kg) (prepared as described in step 2) were heated at 50° C. in dimethylformamide (15 L) for 3 hours. The solution was cooled to 20° C., treated with concentrated hydrochloric acid (7.5 L) and stirred at room temperature for 24 hours. The resulting slurry was diluted with isopropanol (30 L), stirred at room temperature for 30 minutes and then cooled to 0° C. for 1 hour. The solid was collected by filtration and washed with isopropanol (20 L). The solid was dried in vacuo at 40° C. to afford the title compound as a white crystalline solid.

Step, 4: Fluorenylmethyl Glutarate

9-Fluorenyl methanol (2.0 kg), glutaric anhydride (2.33 kg) and sodium bicarbonate (1.71 kg) were stirred together in N-methylpyrrolidinone (8.0 L) at room temperature for 72 hours. The slurry was filtered and the solids washed with isopropyl acetate (2×10.0 L). The filtrate was washed with 1.0 M hydrochloric acid (3×10.0 L). The organic layer was extracted with 1.0 M aqueous sodium hydroxide (3×8.0 L). The combined basic extracts were covered with isopropyl acetate (20.0 L) and acidified to pH 2 with 2.0 M hydrochloric acid (12.5 L). The phases were separated and the aqueous phase was extracted with isopropyl acetate (10.0 L).

The combined organic phases were washed with water (10.0 L) and dried by azeotropic distillation at <60° C. under reduced pressure (KF <0.05%). The solution was then concentrated under reduced pressure (<60° C.) to a volume of 7.0 L. The solution was diluted with hexane (6.0 L), seeded and stirred at room temperature for 30 minutes. The resulting slurry was diluted by addition of hexane (42.0 L) over 40 minutes. The slurry was cooled to 0° C. for 1 hour and the solid collected by filtration and washed with cold (0° C.) 8:1 hexane/iPAC (20.0 L). The solid was dried in vacuo at 45° C. to afford the title compound as a pale cream solid.

Step 5: Fluorenylmethyl Glutarate Pentafluorophenyl Ester

Fluorenylmethyl glutarate (2.5 kg) (prepared as described in Step 4) and pentafluorophenol (1.63 kg) were dissolved in ethyl acetate (25 L). The solution was treated with a solution of dicyclohexylcarbodiimide (1.83 kg) in ethyl acetate (7.5 L) and the mixture was stirred at 20° C. overnight. The resulting slurry was filtered and the solids were washed through with ethyl acetate (10 L). The filtrate was evaporated at atmospheric pressure to a volume of 7.5 L and diluted with hexane (75 L). The slurry was filtered at 60–65° C. then allowed to cool to room temperature and stirred overnight. The slurry was cooled to 0° C. for 1 hour, the solid collected by filtration and washed with 10:1 hexane/ethyl acetate (15 L). The solid was dried in vacuo at 45° C. to afford the title compound as a white crystalline solid.

Step 6: N-(N'-(Fm-Glutaryl)-trans-4-hydroxy-L-prolinyl-alanyl)serine

N-(trans-4-hydroxy-L-prolinyl-alanyl)serine hydrochloride (2.3 kg) (prepared as described in Step 3) was suspended in dimethylformamide (22 L) and the slurry was treated with N-ethylmorpholine (911 ml) followed by a solution of fluorenylmethyl glutarate pentafluorophenyl ester (3.5 kg) (prepared as described in Step 5) in dimethylformamide (14 L). The mixture was heated at 50° C. for 3 hours and the resulting solution evaporated to residue under reduced pressure. The residue was partitioned between water (80 L) and tert-butyl methyl ether (34 L). The phases were separated and the aqueous layer was extracted with tert-butyl methyl ether (34 L). The aqueous solution was seeded and stirred at room temperature overnight. The solid was collected by filtration (slow) and washed with water (25 L). The damp filter cake was dissolved in isopropanol (90 L) with warming and the solution concentrated to half volume by distillation at atmospheric pressure. Additional portions of isopropanol (3×45 L) were added and the batch was concentrated to ca half volume by atmospheric distillation after addition of each portion (Final KF of liquors <0.5%). The slurry was diluted with isopropanol (23 L), stirred at 20° C. overnight, cooled to 0° C. for 1 hour and the solid collected by filtration. The cake was washed with isopropanol (20 L) and the solid dried in vacuo at 45° C. to afford the crude product as a white solid.

Step 7: Recrystallisation of N-(N'-(Fm-Glutaryl)-trans-4-hydroxy-L-prolinyl-alanyl)serine N-(N'-(Fm-Glutaryl)-trans-4-hydroxy-L-prolinyl-alanyl)serine (3.4 kg) (prepared as described in Step 6) was dissolved in methanol (51 L) at reflux. The solution was filtered and concentrated by atmospheric distillation to a volume of 17 L (5 ml/g). The solution was diluted with ethyl acetate (102 L) allowed to cool to 20° C. and stirred overnight. The resulting slurry was cooled to 0° C. for 1 hour and the solid was collected by filtration. The cake was washed with cold (0° C.) 10:1 ethyl acetate/methanol (20 L). and dried in vacuo at 45° C. to afford the product as a white solid.

EXAMPLE 2

Preparation N-(cyclohexylglycyl-glutaminyl-serinyl) leucine Benzyl Ester Hydrochloride (SEQ.ID.NO.: 63)

Step 1: N-(Serinyl)leucine Benzyl Ester Hydrochloride

Leucine benzyl ester p-tosylate (1000 g) and HOBt (412 g) were slurried in isopropyl acetate (12 L). The mixture was cooled to 0° C. in an ice-bath and a slurry of sodium bicarbonate (469.7 g) in water (1 L), N-BOC-L-serine (573.6 g) in water (2 L) and EDC.HCl (560.2 g) in water (2 L) were added. The mixture was allowed to warm to 20° C. over 30 minutes and aged at 20° C. for 2 hours (<1 A % Leu-OBn remaining). If the reaction was not complete after 2 hours, further NaHCO$_3$ and EDC.HCl were added. The phases were separated and the organic layer was washed sequentially with saturated sodium bicarbonate (2×3.75 L), 0.5 M sodium hydrogen sulphate (2×3.75 L) and water (2×2.5 L).

The wet, isopropyl acetate solution was concentrated under reduced pressure to 3 L and the water content checked. (KF=0.12%. It is important that this solution is dry prior to the addition of hydrogen chloride in isopropyl acetate). The solution was transferred to a 20 L round bottom flask under a nitrogen atmosphere and cooled to 0° C. To the solution was added 3.6 M HCl in isopropyl acetate (7 L, 10 mol equiv. HCl). The product began to crystallise after 5 minutes. The reaction was aged at 0° C. for 1 hr, and then allowed to warm to room temperature.

The slurry was cooled to 0–5° C., diluted with heptane (2.5 L) and aged at 0° C. for 30 minutes. The product was collected by filtration, washed with cold isopropyl acetate/heptane (4:1) (2.5 L) and dried in vacuo at 35° C., with a nitrogen sweep.

Step 2: N-(N'-(Boc)-glutaminyl-serinyl)leucine Benzyl Ester

N-(serinyl)leucine benzyl ester hydrochloride (350 g) (prepared as described in Step 1), HOBt (157.7 g) and N-Boc-L-glutamine (262.5 g) were slurried in DMF (2.5 L) and the mixture was cooled to 0° C. N-Ethylmorpholine (245.5 g) and EDC.HCl (214 g) were added and the mixture was aged at 0° C. for 2.5 hours. Water (14.7 L) was added over 20 minutes and the white slurry aged at 0° C. for 1 hour. The product collected by filtration and washed with water (3.2 L). The cake was dried in the fume-hood overnight. The isolated N-BOC-Gln-Ser-Leu-OBn, which contained DMF and HOBt, was combined with a second batch of identical size, and swished in water (12 L) at 20° C. for 1 hour. The product was collected by filtration, washed with water (2.5 L) and air-dried in a fume-hood over the weekend. The batch was dried in vacuo, at 42° C., with a nitrogen bleed.

Step 3: N-(glutaminyl-serinyl)leucine Benzyl Ester Hydrochloride

N-(N'-(Boc)-glutaminyl-serinyl)leucine benzyl ester (715 g, 1.33 M) (prepared as described in Step 2) was suspended in iPAC (3.5 L) at room temperature. To the slurry was added a 3.8 M solution of HCl in iPAC (3.5 L, 13.3 M) whereupon all the solids dissolved. After a short time, the product crystallised. The mixture was stirred at room temperature for 3.75 hours when HPLC showed complete reaction. The slurry was diluted with iPAC (4.0 L), stirred for 1 hour at room temperature and the solid collected by filtration under nitrogen. The product is very hygroscopic in the presence of excess HCl and must be collected under dry nitrogen.

The cake was washed with iPAC (4.0 L), the solid dried on the filter under nitrogen for 2 hours and then dried in vacuo at 45° C.

Step 4: N-(N'-(Boc)-cyclohexylglycylglutaminyl-serinyl)leucine Benzyl Ester ((SEQ.ID.NO.: 64)

N-(glutaminyl-serinyl)leucine benzyl ester hydrochloride (2.6 kg) (prepared as described in Step 3), N-Boc-L-cyclohexylglycine (1.414 kg) and HOBt hydrate (168 g) were dissolved in DMF (13.0 L). N-ethylmorpholine (1.266 kg, 11.0 M) and EDC hydrochloride (1.265 kg) were added and the mixture stirred at 20° C. for 3 hours. The solution was diluted with ethyl acetate (13.0 L) and water (26.0 L) added. The product precipitated and the slurry was stirred at room temperature for 1 hour. The solid was collected by filtration, washed with 1:1 ethyl acetate/water (60 L) dried on the filter under nitrogen for 24 hours and dried in vacuo at 45°. The title compound was obtained as a white solid.

Step 5: N-(cyclohexylglycyl-glutaminyl-serinyl)leucine Benzyl Ester Hydrochloride (SEQ.ID.NO.: 63)

N-(N'-(Boc)-cyclohexylglycylglutaminyl-serinyl)leucinebenzyl ester (1850 g) (prepared as described in Step 4) was slurried in isopropyl acetate (3.2 L). The slurry was cooled to 0° C. in an ice bath and 3.8 M HCl/isopropyl acetate (3.7 L, 11.4 mol equiv.) was added over 5 minutes, maintaining the temperature between 8 and 10° C. The starting material had dissolved after 15–20 minutes. The solution was seeded and the reaction aged at 8–10° C. for 2 hrs, (<1A % N-Boc-tetrapeptide-OBn remaining). The batch was filtered, under a nitrogen blanket, washed with cold (10° C.) isopropyl acetate (4×3 L) then dried on the filter under nitrogen. The solid was dried in vacuo, at 40° C.

The crude N-(cyclohexylglycyl-glutaminyl-serinyl)leucine benzyl ester hydrochloride (2.2 Kg) was slurried in methanol (22.3 L) at room temperature. The batch was stirred for 1 hour and then ethyl acetate (44.6 L) was added over 30 minutes. The batch was cooled to 0–5° C., aged for one hour, then filtered and washed with cold (0–5° C.) methanol/ethyl acetate (6 L, 1:2). The solid was dried on the filter, under nitrogen, for 45 minutes and then dried in vacuo, at 40° C., with a nitrogen sweep.

The N-(cyclohexylglycyl-glutaminyl-serinyl)leucine benzyl ester hydrochloride (1.478 Kg) was slurried in methanol (14.8 L) at room and the batch stirred for 1 hr. Ethyl acetate (29.6 L) was added over 30 minutes, the batch was cooled to 0–5° C. and aged for an hour. The solid collected by filtration, washed with cold (0–5° C.) methanol/ethyl acetate (4.5 L, 1:2), dried on the filter for 45 minutes, under nitrogen, and then dried under vacuum, at 40° C. This material was then utilized in subsequent reactions.

EXAMPLE 3

Preparation N-(N'-(Fm-Glutaryl)-trans-4-hydroxy-L-prolinyl-alanyl-serine-yclohexylglycyl-glutaminyl-serinyl)leucine (heptapeptide 2) (SEQ.ID.NO.: 52)

Step 1: N-(N'-(Fm-Glutaryl)-trans-4-hydroxy-L-prolinyl-alanyl-serine-cyclohexylglycyl-glutaminyl-serinyl)leucine Benzyl Ester (SEQ.ID.NO.: 67)

N-(cyclohexylglycyl-glutaminyl-serinyl)leucine benzyl ester hydrochloride (500 g) (prepared as described in Example 2), N-(N'-(Fm-Glutaryl)-trans-4-hydroxy-L-prolinyl-alanyl)serine (490 g) (prepared as described in Example 1) and HOAt (160 g) were slurried in DMF (8.2 L) and cooled to 2° C. in an ice bath. N-ethylmorpholine (135 ml) was added followed by EDC.HCl (210 g). The mixture was stirred at 0–2° C. for 2 hours and sampled. HPLC showed 0.2A % tetrapeptide remaining. The reaction mixture was diluted with ethyl acetate (4 L) and transferred to a 30-gallon glass vessel through a 5µ in-line filter. The flask and lines were rinsed with ethyl acetate/DMF (1:1, 500 ml) and ethyl acetate (4 L). Water (16.4 L) was added over 25 minutes (temperature 11° C. to 23° C.) and the mixture stirred slowly, at 20° C., for 30 minutes. The product was collected by filtration, washed with water (3 L), ethyl acetate (1 L) and water (2×3 L), then dried on the filter under nitrogen, and dried in vacuo at 45° C.

Step 2: N-(N'-(Fm-Glutaryl)-trans-4-hydroxy-L-prolinyl-alanyl-serine-cyclohexylglycyl-glutaminyl-serinyl)leucine (SEQ.ID.NO.: 52)

N-(N'-(Fm-Glutaryl)-trans-4-hydroxy-L-prolinyl-alanyl-serine-cyclohexylglycyl-glutaminyl-serinyl)leucine benzyl ester (1.1 Kg) (prepared as described in Step 1) was dissolved in dimethylacetamide (7.8 L) containing methanesulphonic acid (93.5 ml). 5% Pd/C (110 g, 10 wt %), slurried in DMA (1.0 L), was added and the mixture hydrogenated at atmospheric pressure for 1 hour 40 minutes. The reaction mixture was sampled: HPLC showed no starting material remaining.

The reaction mixture was filtered through a pre-wetted (DMA) pad of hyflo (500 g) to remove the catalyst. The hyflo pad washed with DMA (2.2 L) and then ethyl acetate (5.5 L). The filtrate was diluted with ethyl acetate (5.5 L) and stirred for 15 minutes. Water (44 L) was added over 40 minutes and the batch age for 1 hour. The solid collected by filtration, washed with water (1×10 L, 3×20 L), dried on the filter under a nitrogen blanket and dried in vacuo at 45° C.

Step 3: N-(N'-(Fm-Glutaryl)-trans-4-hydroxy-L-prolinyl-alanyl-serine-cyclohexylglycyl-glutaminyl-serinyl)leucine Swish Purification Crude N-(N'-(Fm-Glutaryl)-trans-4-hydroxy-L-prolinyl-alanyl-serine-cyclohexylglycyl-glutaminyl-serinyl)leucine (2.58 kg) (prepared as described in Step 2) was sieved.

The solid (2.56 Kg) was swished in ethyl acetate for 3 hours. The solid was collected by filtration, washed with ethyl acetate (26 L), dried on the filter under nitrogen and dried in vacuo at 40° C.

EXAMPLE 4

Preparation of [N-Glutaryl(OFm)-(4-trans-L-Hyp)]-Ala-Ser-Chg-Gln-Ser-Leu-Dox Compound 3 (SEQ.ID.NO.: 54)

To a 3 necked, 12 L round bottom flask equipped with mechanical stirrer, thermocouple, and nitrogen inlet was charged DMF (5.1 L) and HOAt (43.4 g, 319 mmoles, 1.2 equivalents). The yellow solution was inerted with nitrogen and warmed to 40° C. Heptapeptide 2 (357.34 g, 266 mmoles) was added portion-wise to the warm solution; after stirring for 30 minutes at 40° C., a light yellow, opaque, homogeneous mixture resulted.

The mixture was cooled to room temperature, Doxorubicin 1 was added (158.9 g, 274 mmoles, 1.03 equivalents), and the red slurry was further cooled to −5° C. One equivalent of 2,4,6-collidine (35 ml) was added followed by 0.8 equivalents of EDC (40.8 g, 213 mmoles) followed by the remaining two equivalents of 2,4,6-collidine (70 ml). The red slurry was aged at −5° C. to −3° C.

After aging for a total of 3 hours, conversion had reached 90 A % Compound 3, 2.5 A % peptide 1 and the reaction was warmed to 0° C. Aging for another 2 hours reduced peptide level to 0.73 A % and the reaction was quenched as follows.

In a 50 L, 4 necked round bottom flask equipped with a mechanical stirrer, thermocouple, and nitrogen inlet, was charged $K_2HPO_4$ (67.9 g), $KH_2PO_4$ (283 g), and water (13 L) to give a 0.19 M pH 6.3 buffer solution. The buffer solution was inerted with nitrogen, cooled to 15–18° C., and the cold reaction mixture (−1° C.) was added to the buffer via an addition funnel over 60 minutes maintaining the slurry temperature at 15–18° C. After complete addition, the red slurry was aged 15 minutes at 18° C., and filtered. The filter cake was displacement washed with water (1×6 L), followed by slurry washing with water (6×6 L), and dried in vacuo at room temperature with a nitrogen sweep. After drying for 48 hours, 402 g (96% yield based on weight) of red solid was obtained. The solid was assayed to have an HPLC purity of 93.54 A %.

EXAMPLE 4A

Alternate Preparation of [N-Glutaryl(OFm)-(4-trans-L-Hyp)]-Ala-Ser-Chg-Gln-Ser-Leu-Dox Compound 3 (SEQ.ID.NO.: 54)

DMF (400 mL) was charged to a 1 L RB flask and degassed by $N_2$ sparge while cooling to −6° C. The peptide (19.97 g, 19.06 mmol) and HOAt (3.12 g, 22.9 mmol) were then charged as solids to the cold DMF. A slurry of doxorubicin HCl (11.05 g, 19.06 mmol) in degassed DMF (50 mL) was charged by vacuum, followed by two rinses (2×25 mL) of the slurry flask. 2,4,6-collidine was charged followed by a portion of EDC (2.92 g, 0.8 eq.). After 1.3 h, a second charge of EDC (2.19 g, 0.6 eq) was made. After a total age of 7.4 h the clear red solution was queched by dropwise addition to a pH 6.2 phosphate buffer (1350 mL) at 16–17° C. over 1.3 h. The resulting slurry was filtered and the filter cake was then washed with water (2000 mL). The filter cake was dried under a $N_2$ stream giving 28.7 g red powder (95.6%, uncorrected for purity).

EXAMPLE 4B

Alternate Preparation of [N-Glutaryl(OFm)-(4-trans-L-Hyp)]-Ala-Ser-Chg-Gln-Ser-Leu-Dox Compound 3 (SEQ.ID.NO.: 54)

A 1 L, 4 neck round bottom flask was set up and 20.0 g of Doxorubicin. HCl (20.0 g, 34.5 mmol) was added in a glovebox. The flask was then equipped with a truebore stirrer, $N_2$ inlet/vacuum inlet, and a thermocouple. DMF (472 mL) and water (4.7 mL) were premixed (20° C.) and then charged to form a red slurry. The 2,4,6-collidine (12.5 g, 103 mmol) and 2-HOPO (4.6 g, 41.4 mmol) were then, respectively, charged at ambient temperature and allowed to mix for 10 minutes. The slurry was then cooled to −5° C. and the heptapeptide 2 (40.6 g, 35.3 mmol) was charged. It was stirred for 30 minutes at that temperature. The first, 0.8 equivalent of the EDC.HCl (5.3 g) was charged, and the solution allowed to mix for 90 minutes. The reaction was monitored by HPLC.

After 90 minutes had elapsed, the remaining 0.6 equivalents of EDC.HCl (3.96 g) was added, the cooling bath was removed and the reaction was allowed to mix overnight at room temperature (21–22° C.).

The prepared buffer solution (1.20 L of the following buffer: 10.9 g $K_2HPO_4$, 43.54 g $KH_2PO_4$; pH 6.05) was added to a 3-L round bottom flask equipped with a truebore stirrer, $N_2$ inlet and thermocouple. The reaction solution was transferred to a 1-L addition funnel while, concurrently, the temperature of the buffer was reduced to 15–18° C.

The reaction solution was added to the buffer over 1–1.5 hours, while maintaining the temperature between 15–18° C. A precipitate resulted. The precipitated material was filtered and washed with water (2.30 L).

After drying overnight at 22° C. under $N_2$ and house vacuum, the solid (53.0 g) was assayed and was 91.5 A %, 88.1 wt. %. The yield after correction for purity was 86%.

EXAMPLE 4C

Alternate Preparation of [N-Glutaryl(OFm)-(4-trans-L-Hyp)]-Ala-Ser-Chg-Gln-Ser-Leu-Dox Compound 3 (SEQ.ID.NO.: 54)

A 3 L, 4 neck round bottom flask was set up and, concurrently, 20.0 grams of Doxorubicin.HCl (34.5 mmol) was added in a glovebox to a sealed beaker or Erlenmeyer flask. The 3 L flask was then equipped with a truebore stirrer, $N_2$ inlet/vacuum inlet, and a thermocouple. DMF (472 mL) and water (4.7 mL) were premixed (20° C.) and then partially charged (approximately ½ the volume) to the 3 L vessel. 2-HOPO (4.6 g, 41.4 mmol) and HOAt (0.47 g, 3.45 mmol) were then, respectively, charged and allowed to mix for 10 minutes or until dissolved. One-quarter of the wet DMF was then added to the Dox.HCl to form a slurry, and this was then added to the 3 L vessel. Finally, the 2,4,6-collidine (12.5 g, 103 mmol) was added to the 3 L vessel which was then cooled to −5° C. and the heptapeptide 2 (40.6 g, 35.3 mmol) was charged. After stirring for 30 minutes the first, 0.8 equivalents of the EDC.HCl was charged (5.3 g), followed by the final quarter of solvent. The resulting slurry was stirred for about 90 minutes and then the remaining 0.6 equivalents of EDC.HCl (3.96 g) was added. The cooling bath was removed and the reaction was allowed to mix overnight at room temperature (21–22° C.). Ethyl acetate (354 mL) was then added to, the reaction solution at 20° C.

The temperature of the reaction solution was reduced to 15–18° C. The pH6 buffer solution (1.20 L of water, 10.9 g $K_2HPO_4$, 43.54 g $KH_2PO_4$) was added slowly to the reaction solution over 1 hour, while maintaining the temperature between 15 and 18° C.

The precipitated material was filtered through a 600 mL medium sintered glass funnel, washed with water. (2.3 L) and the cake was dried overnight on the filter at ambient temperature under $N_2$. The solid (54.5 g) was assayed at 89.7 A %. The yield, after correction for purity, was 90.0%.

EXAMPLE 5

Preparation of [N-Glutaryl-(4-trans-L-Hyp)]-Ala-Ser-Chg-Gln-Ser-Leu-Dox Piperidinium salt Compound 4 (SEQ.ID.NO.: 51)

To a 3 necked, 12 L round bottom flask equipped with mechanical stirrer, thermocouple, and nitrogen inlet was charged Compound 3 (399 g, 253.5 mmoles, TG 1.4%) and DMF (3.55 L). The red solution was inerted with nitrogen, cooled to 1° C., and a solution of piperidine (40 mL, 404 mmoles, 1.6 eq.) in DMF (400 mL) was added drop-wise over 70 minutes maintaining the batch temperature at 0–2° C.

The reaction was monitored by HPLC. After aging 1.5 hours at 0–2° C., conversion had reached 92.4%. Additional piperidine was charged after 2 hours reaction time (2.5 mL piperidine in 25 mL DMF); after aging another 2 hours, conversion had reached 98.1% and the reaction was quenched as follows.

In a 22 L, 3 necked round bottom flask equipped with mechanical stirrer, thermocouple, and nitrogen inlet was charged isopropyl acetate (12.1 L), inerted with nitrogen, and cooled to 0–5° C. To the cold i-PAc was added the cold (2° C.) reaction mixture via nitrogen pressure cannulation over 40 minutes. The resulting pink slurry was aged at 0–5° C. for thirty minutes then filtered under nitrogen. The cake was displacement washed with i-PAc (2×4 L) then slurry washed with i-PAc (3×4 L). All washes were done under a nitrogen blanket. The solid was dried in vacuo at room temperature with a nitrogen sweep for 24 hours to give 369.05 g of an orange solid. The solid was assayed by HPLC, 87 A %.

EXAMPLE 6

Preparative HPLC Purification of [N-Glutaryl-(4-trans-L-Hyp)]-Ala-Ser-Chg-Gln-Ser-Leu-Dox Piperidinium salt Compound 4 (SEQ.ID.NO.: 51)

The crude piperidine salt was purified by preparative HPLC on C-18 silica gel, eluting with a 0.1% aqueous ammonium acetate/acetonitrile gradient (100% $NH_4OAc$ to 55% $NH_4OAc$ over 80 min). The rich cuts that were >97% pure were pooled and rechromatographed on C-18 silica gel using a 2% aqueous HOAc/acetonitrile gradient (100% aqueous HOAc to 40% aqueous HOAc over 60 min). The fractions that were >98% pure were pooled and lyophilized, providing the pure free acid 4.

EXAMPLE 6A

Alternate Preparation of [N-Glutaryl-(4-trans-L-Hyp)]-Ala-Ser-Chg-Gln-Ser-Leu-Dox Compound 4 (SEQ.ID.NO.: 51)

To a solution of the heptapeptide 2 (1.09 g, 0.99 mmol) in DMF at 0° C. was added solid quinuclidine (0.34 g, 3.00 mmol). The solution was stirred at 0° C. for 0.5 h, and at 20° C. for 2.0 h, respectively. An aliquot was taken and assayed by LC to show no heptapeptide 2 remained, indicating that conversion to the diacid was complete.

To this solution of [N-Glutaryl-(4-trans-L-Hyp)]-Ala-Ser-Chg-Gln-Ser-Leu was added 2,4,6-collidine (0.50 mL, 3.78 mmol), HOAt (0.163 g, 3.00 mmol) and Doxorubicin.HCl (0.58 g, 1.00 mmol), resulting in a slurry. The slurry was cooled to 0° C. and solid EDC.HCl (0.20 g, 1.04 mmol) was introduced in one portion. The reaction was aged for 2.5 h at 0° C. to lead to a homogenous solution that was assayed by LC to show the formation of Compound 4 in 78% yield.

EXAMPLE 6B

Alternate Preparation of [N-Glutaryl-(4-trans-L-Hyp)]-Ala-Ser-Chg-Gln-Ser-Leu-Dox Compound 4 (SEQ.ID.NO.: 51)

To a solution of the heptapeptide 2 (1.09 g, 0.99 mmol) in DMF at 0° C. was added a solid quinuclidine (0.34 g, 3.00 mmol). The solution was stirred at 0° C. for 0.5 h, and at 20° C. for 2.0 h, respectively. An aliquot was taken and assayed by LC to show no heptapeptide 2 remained, indicating that conversion to the diacid was complete.

To a portion of the solution of [N-Glutaryl-(4-trans-L-Hyp)]-Ala-Ser-Chg-Gln-Ser-Leu (ca. 0.497 mmol) was added 2,4,6-collidine (0.123 mL, 0.934 mmol), 2-HOPO (52 mg, 0.467 mmol) and Doxorubicin.HCl (092 mg, 0.159 mmol) at 20° C., resulting in a slurry. The slurry was cooled to 0° C. and solid EDC.HCl (100 mg, 0.524 mmol) was introduced in one portion. The reaction was aged for 2.0 h at 0° C. and then assayed by LC to show the formation of Compound 4 in 93.9% yield and no remaining doxorubicin.

Alternative Preparation of N-(N'-(Fm-Glutaryl)-trans-4-hydroxy-L-prolinyl-alanyl-serine-cyclohexylglycyl-glutaminyl-serinyl)leucine (SEQ.ID.NO.: 52)

Fm-Glutaryl-Hyp-Ala-Ser-Chg-Gln-Ser-Leu-OBn (prepared as described in Step 1 or Alternate Step 1) (200 g) was dissolved in dimethylacetamide (1.9 L) at 45–50° C. 5% Pd/C (20 g, 10 wt %) slurried in DMA (100 ml) was added and the slurry was cooled to −5 to −10° C. The mixture was hydrogenated at atmospheric pressure maintaining the temperature between −10 and −5° C. for 5.5 hours.

The mixture was filtered while cold through a pre-wetted pad of Hyflo. The filtrate was diluted with ethyl acetate (2.5 L) and water (8.0 L) was added. The batch was aged for a further 1 hour and the solid was collected by filtration. The cake was washed with water and sucked down on the filter and then dried in vacuo at 45° C. with a nitrogen sweep.

What is claimed is:

1. A process for the preparation of a compound of formula I:

or a pharmaceutically acceptable salt thereof
wherein
  oligopeptide is an oligopeptide which is selectively recognized by the free prostate specific antigen (PSA) and is capable of being proteolytically cleaved by the enzymatic activity of the free prostate specific antigen,
  $R^a$ is —$CH_3$, —$CH_2OH$, —$CH_2OCO(CH_2)_3CH_3$, or —$CH_2OCOCH(OC_2H_5)_2$;
  $R^b$ is —$OCH_3$, —OH or —H;
  $R^d$ is —OH, —OTHP or —H; and
  $R^e$ is —OH or —H, provided that $R^e$ is not —OH when $R^d$ is —OH or —OTHP;
  R is selected from:
    a) acetyl;
    b) 
    c) 
    d) 
    e) hydrogen;
  $R^1$ and $R^2$ are independently selected from:
    a) hydrogen,
    b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^3O$—, $R^3C(O)NR^3$—, $(R^3)_2NC(O)$—, $R^3_2N$—$C(NR^3)$—, $R^4S(O)_mNH$, CN, $NO_2$, $R^3C(O)$—, $N_3$, —$N(R^3)_2$, or $R^4OC(O)NR^3$—,
    c) unsubstituted $C_1$–$C_6$ alkyl,
    d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^3O$—, $R^4S(O)_mNH$, $R^3C(O)NR^3$—, $(R^3)_2NC(O)$—, $R^3_2N$—$C(NR^3)$—, CN, $R^3C(O)$—, $N_3$, —$N(R^3)_2$, and $R^4OC(O)$—$NR^3$—; or
  $R^1$ and $R^2$ are combined to form —$(CH_2)_s$— wherein one of the carbon atoms is optionally replaced by a moiety selected from: O, $S(O)_m$, —NC(O)—, NH and —$N(COR^4)$—;
  $R^3$ is selected from: hydrogen, aryl, substituted aryl, heterocycle, substituted heterocycle, $C_1$–$C_6$ alkyl and $C_3$–$C_{10}$ cycloalkyl;
  $R^4$ is selected from: aryl, substituted aryl, heterocycle, substituted heterocycle, $C_1$–$C_6$ alkyl and $C_3$–$C_{10}$ cycloalkyl;
  m is 0, 1 or 2;
  n is 1, 2, 3 or 4;
  p is zero or an integer between 1 and 100;
  q is 0 or 1, provided that if p is zero, q is 1;
  r is an integer between 1 and 10; and
  s is 3, 4 or 5;
  that comprises the step of preparing the compound of the formula Ia:

or a salt thereof;
wherein
  oligopeptide, R, $R^a$, $R^b$, $R^d$ and $R^e$ are described as above
  R' is selected from:
    a) R as described above,
    b) a protected precursor to R, and
    c) an N-terminus protecting group;

by mixing an oligopeptide of the formula A:

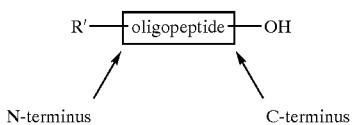

A wherein oligopeptide and R' are described as above; or a salt thereof;
with an anthracycline antibiotic of the formula B:

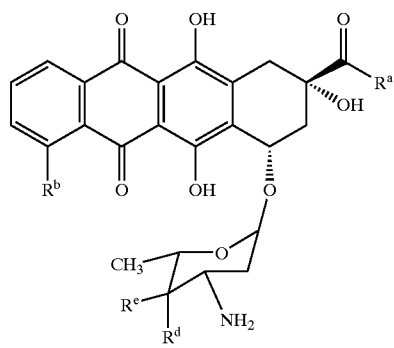

B wherein $R^a$, $R^b$, $R^d$ and $R^e$ are as described hereinabove,
or a salt thereof;
in the presence of a carboxyl activating agent, an additive comprising the combination of HOPO and HOAt and, optionally, in the presence of a base.

2. The process according to claim 1 wherein R' is a protected precursor to R or an N-terminus protecting group and wherein the process further comprises the step of removing the protecting group to produce the compound of the formula I.

3. The process according to claim 1 wherein the oligopeptide of formula A is mixed with a salt of the anthracycline antibiotic of the formula B in the presence of a carboxyl activating agent, an additive comprising the combination of HOPO and HOAt, and a base.

4. The process according to claim 1 wherein the carboxyl activating agent comprises dicyclohexylcarbodiimide (DCC), N-ethyl-N-(3-dimethylaminopropyl)-carbodiimide (EDC), or 1,3-diisopropylcarbodiimide (DIC).

5. The process according to claim 4 wherein the carboxy activating agent is EDC.

6. The process according to claim 3 wherein the base comprises 2,4,6-collidine, lutidine, pyridine, triethyl amine or $(iPr)_2NEt$.

7. The process according to claim 6 wherein the base is 2,4,6-collidine.

8. The process according to claim 1 wherein the oligopeptide of the formula A is mixed with the anthracycline antibiotic of the formula B in the presence of an additive, comprising the combination of HOPO and HOAt, and a base, and a carboxyl activating agent is thereafter added to the mixture.

9. The process according to claim 8 wherein the oligopeptide of the formula A is mixed with the anthracycline antibiotic of the formula B in the presence of an additive, comprising the combination of HOPO and HOAt, and a base, and a carboxyl activating agent is thereafter added to the mixture in two or more portions.

10. The process according to claim 1 wherein the anthracycline antibiotic is doxorubicin ($R^a$ is —$CH_2OH$, $R^b$ is —$OCH_3$, $R^c$ is H and $R^d$ is —OH).

11. The process according to claim 1 wherein R is selected from:

a) acetyl; and
b)

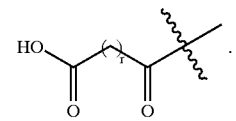

12. The process according to claim 1 wherein R is

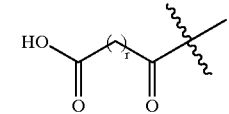

and R' is

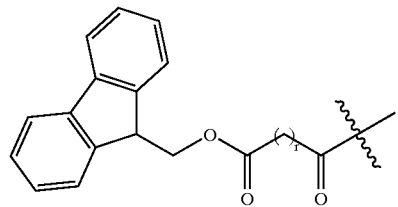

13. The process according to claim 1 wherein R is

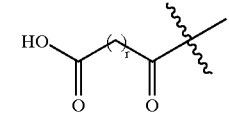

and R' is and wherein the process comprises the step of removing the protecting group by contacting the compound of formula Ia with a base selected from piperidine, dimethyl amine, diethyl amine, pyrrolidine and quinuclidine.

14. The process according to claim 13 wherein the compound of formula Ia is contacted with piperidine.

15. A process for the preparation of the compound of formula 4:

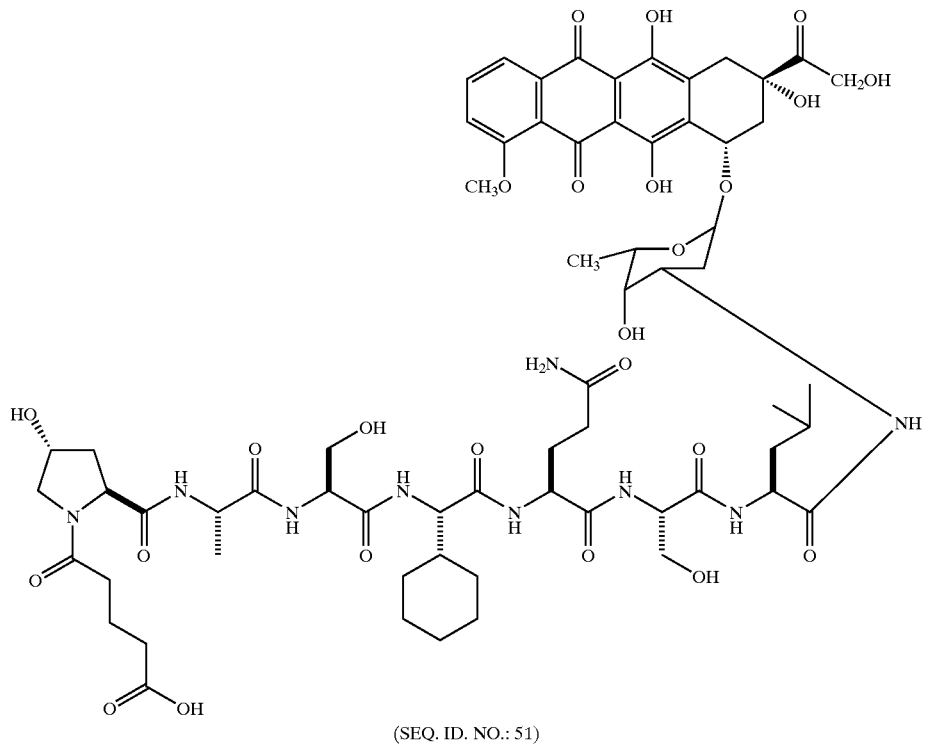
(SEQ. ID. NO.: 51)
or a pharmaceutically acceptable salt thereof;
which comprises the step of mixing an oligopeptide of the formula 2a:
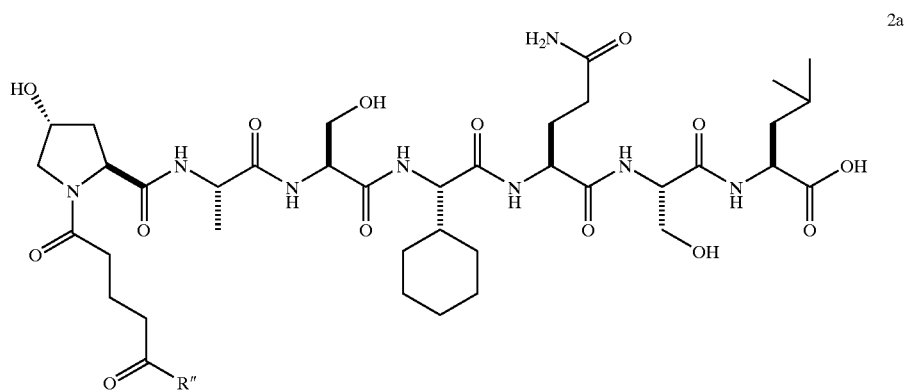
wherein R" is —OH or a protected precursor to —OH;
or a salt thereof;

with an anthracycline antibiotic of the formula 1:

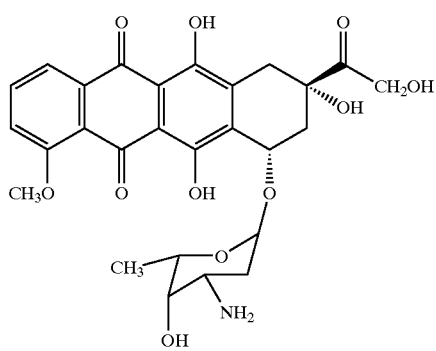

or a salt thereof, in the presence of a carboxyl activating agent, an additive comprising the combination of HOPO and HOAt and, optionally in the presence of a base, to form a compound of the formula 3a

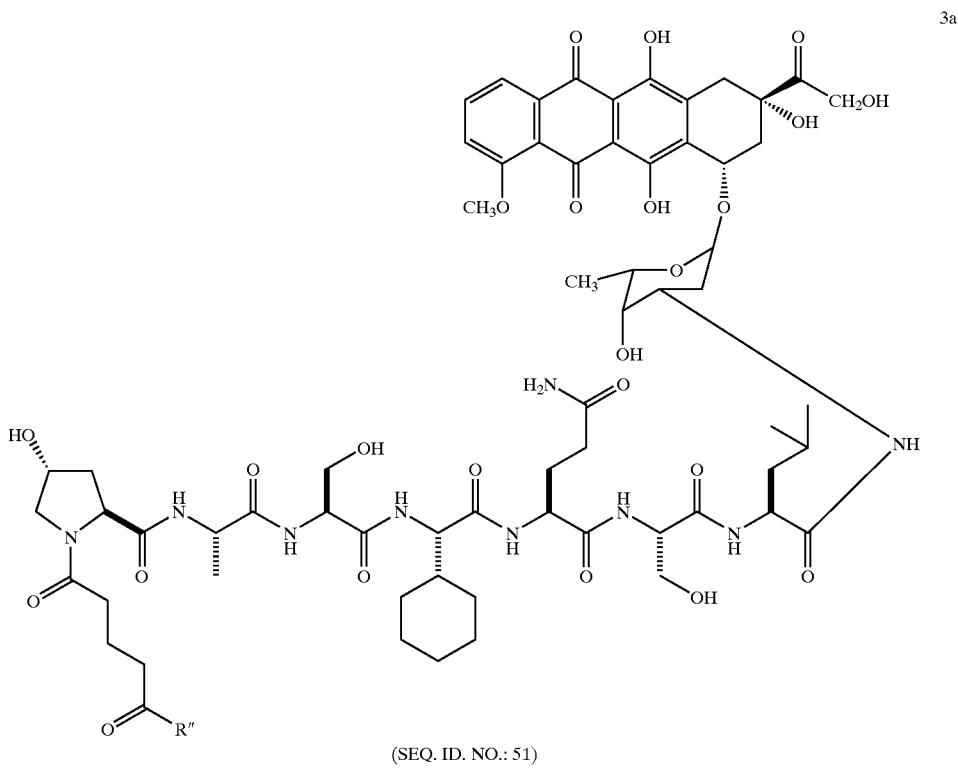

(SEQ. ID. NO.: 51)

or a salt thereof.

16. The process according to claim 15 which further comprises the step of converting R" to an —OH moiety.

17. The process according to claim 15 wherein the carboxyl activating agent comprises dicyclohexylcarbodiimide (DCC), N-ethyl-N-(3-dimethylaminopropyl)-carbodiimide (EDC), or 1,3-diisopropylcarbodiimide (DIC).

18. The process according to claim 17 wherein the carboxy activating agent is EDC.

19. The process according to claim 15 wherein the oligopeptide of formula 2a is mixed with a salt of the anthracycline antibiotic of the formula 1 in the presence of a carboxyl activating agent, an additive comprising the combination of HOPO and HOAt, and a base.

20. The process according to claim 19 wherein the base comprises 2,4,6-collidine, lutidine, pyridine, triethyl amine or (iPr)$_2$NEt.

21. The process according to claim 20 wherein the base is 2,4,6-collidine.

22. The process according to claim 15 wherein the oligopeptide of the formula 2a is mixed with the anthracycline antibiotic of the formula 1 in the presence of an additive, comprising the combination of HOPO and HOAt, and a base, and a carboxyl activating agent is thereafter added to the mixture.

23. The process according to claim 22 wherein the oligopeptide of the formula 2a is mixed with the anthracycline antibiotic of the formula 1 in the presence of an additive, comprising the combination of HOPO and HOAt, and a base, and a carboxyl activating agent is thereafter added to the mixture in two or more portions.

24. A process for the preparation of the compound of formula 4:

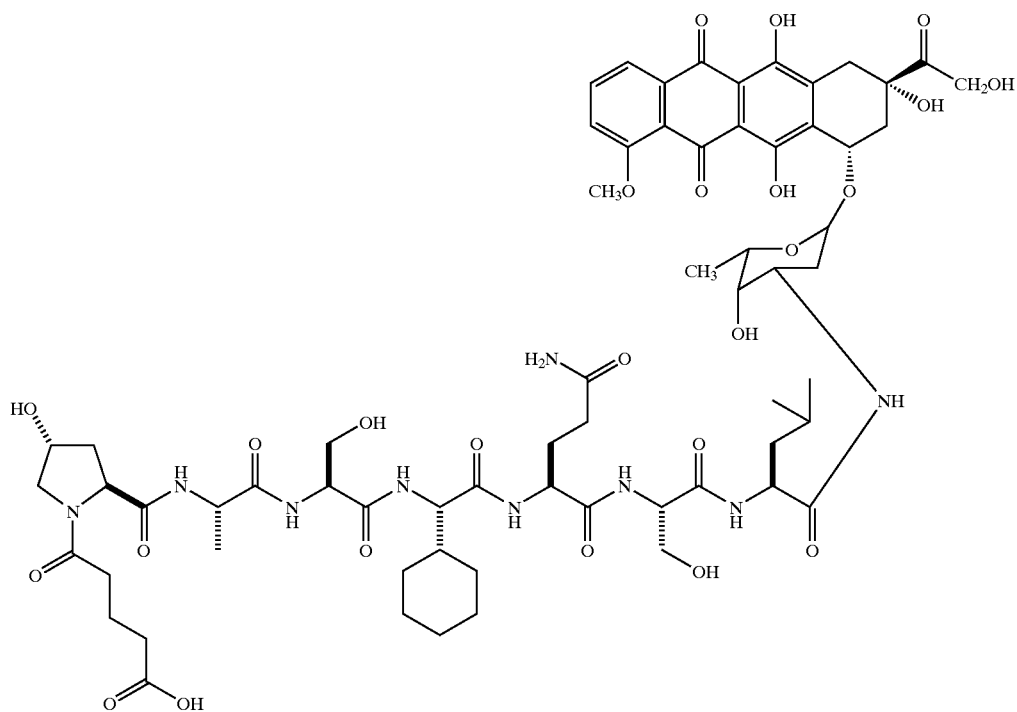
(SEQ.ID.NO.: 51)
or a pharmaceutically acceptable salt thereof;
which comprises the step of mixing an oligopeptide of the formula 2:
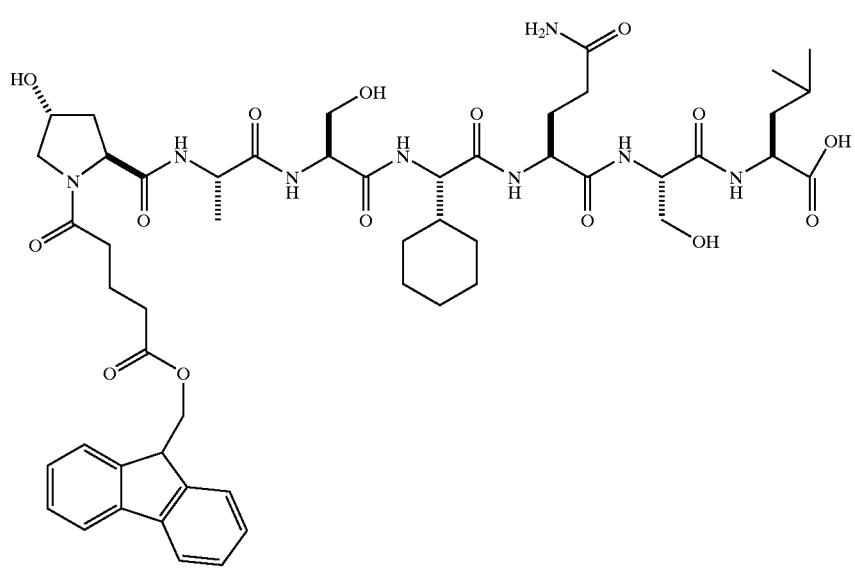
(SEQ.ID.NO.: 52)
or a salt thereof;

with an anthracycline antibiotic of the formula 1:

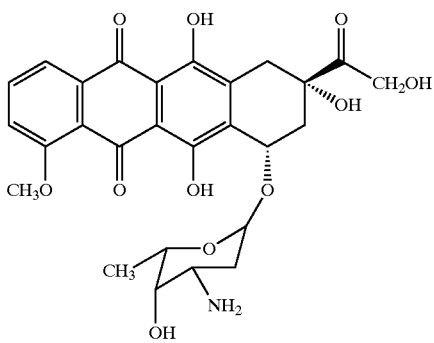

or a salt thereof;
in the presence of a carboxyl activating agent, an additive comprising the combination of HOPO and HOAt and a base to form a compound of the formula 3:

anthracycline antibiotic of the formula 1 is added to the first slurry to form a second slurry.

26. The process according to claim 25 wherein the solvent is DMF.

27. The process according to claim 24 which further comprises the step of removing the fluorenylmethoxy protecting group of the compound of formula 3 to produce the compound of the formula 4.

28. The process according to claim 27 which comprises the step of removing the fluorenylmethoxy protecting group of the compound of formula 3 by contacting the compound of formula 3 with a base selected from piperidine, dimethyl amine, diethyl amine, pyrrolidine and quinuclidine.

29. The process according to claim 28 wherein the compound of formula 3 is contacted with piperidine.

30. The process according to claim 24 wherein the carboxyl activating agent comprises dicyclohexylcarbodiimide (DCC), N-ethyl-N-(3-dimethylaminopropyl)-carbodiimide (EDC), or 1,3-diisopropylcarbodiimide (DIC).

31. The process according to claim 30 wherein the carboxy activating agent is EDC.

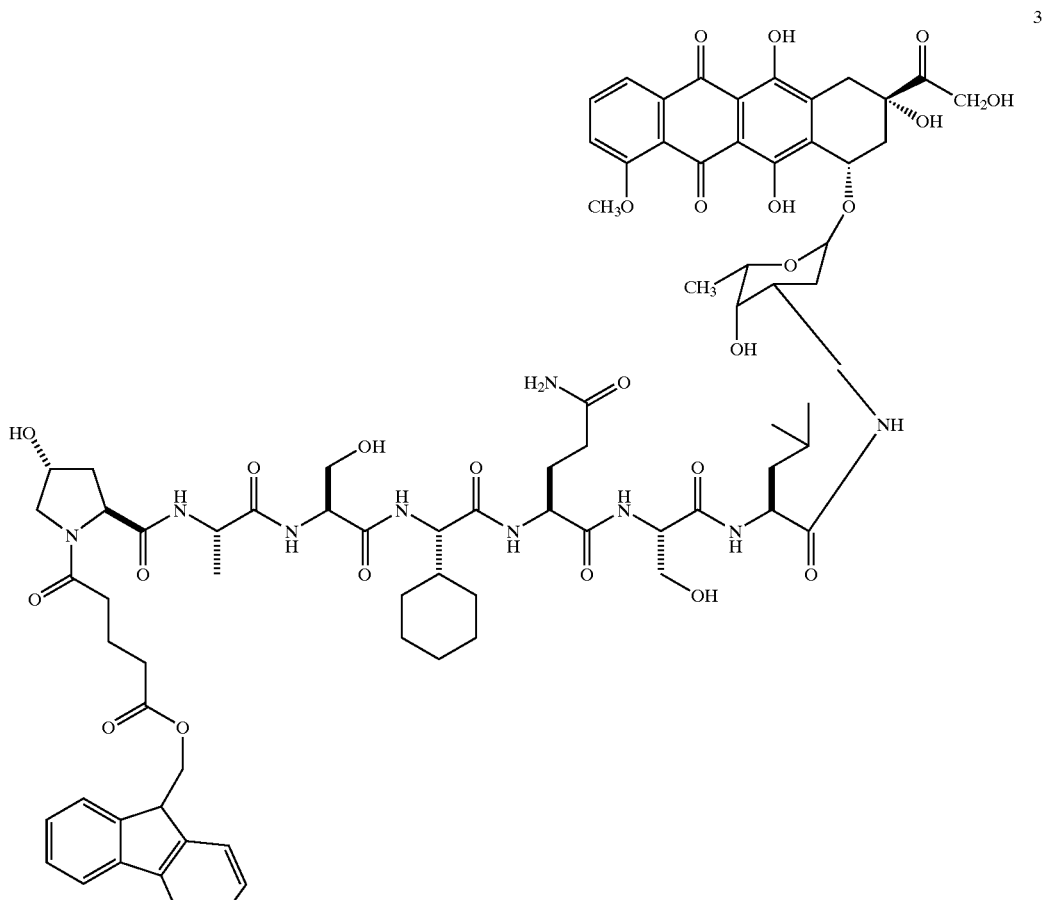

(SEQ.ID.NO.: 52)

or a salt thereof.

25. The process according to claim 24 which comprises adding the oligopeptide of the formula 2 to a reaction mixture that comprises a solvent at a temperature from about −6° C. to about −3° C. to form a first slurry and the 32. The process according to claim 24 wherein the base comprises 2,4,6-collidine, lutidine, pyridine, triethyl amine or (iPr)$_2$NEt.

33. The process according to claim 32 wherein the base is 2,4,6-collidine.

34. The process according to claim 24 wherein the oligopeptide of the formula 2 is mixed with the anthracycline antibiotic of the formula 1 in the presence of an additive, comprising the combination of HOPO and HOAt, and a base, and a carboxyl activating agent is thereafter added to the mixture.

35. The process according to claim 34 wherein the oligopeptide of the formula 2 is mixed with the anthracycline antibiotic of the formula 1 in the presence of an additive, comprising the combination of HOPO and HOAt, and a base, and a carboxyl activating agent is thereafter added to the mixture in two or more portions.

* * * * *